United States Patent
Kano

(10) Patent No.: US 9,271,699 B2
(45) Date of Patent: Mar. 1, 2016

(54) ULTRASONIC DEVICE, PROBE, ELECTRONIC INSTRUMENT, DIAGNOSTIC DEVICE, AND PROCESSING DEVICE

(71) Applicant: SEIKO EPSON CORPORATION, Tokyo (JP)

(72) Inventor: Kazuyuki Kano, Aichi (JP)

(73) Assignee: Seiko Epson Corporation, Tokyo (JP)

( * ) Notice: Subject to any disclaimer, the term of this patent is extended or adjusted under 35 U.S.C. 154(b) by 278 days.

(21) Appl. No.: 13/771,605

(22) Filed: Feb. 20, 2013

(65) Prior Publication Data

US 2013/0226005 A1    Aug. 29, 2013

(30) Foreign Application Priority Data

Feb. 24, 2012    (JP) ................................ 2012-038360

(51) Int. Cl.
*A61B 8/00* (2006.01)
*B06B 1/00* (2006.01)
*B06B 1/06* (2006.01)

(52) U.S. Cl.
CPC ............ *A61B 8/4494* (2013.01); *A61B 8/4411* (2013.01); *B06B 1/0607* (2013.01); *B06B 1/0622* (2013.01); *A61B 8/4444* (2013.01)

(58) Field of Classification Search
None
See application file for complete search history.

(56) References Cited

U.S. PATENT DOCUMENTS

| | | | | |
|---|---|---|---|---|
| 4,233,623 A | * | 11/1980 | Pavliscak | 348/797 |
| 5,017,989 A | * | 5/1991 | Street et al. | 257/291 |
| 6,219,113 B1 | * | 4/2001 | Takahara | 349/42 |
| 2004/0201551 A1 | * | 10/2004 | Suzuki | H01J 11/12 345/55 |
| 2008/0067895 A1 | * | 3/2008 | Adachi et al. | 310/324 |
| 2009/0079684 A1 | * | 3/2009 | Watanabe | 345/92 |
| 2010/0198070 A1 | | 8/2010 | Asafusa et al. | |
| 2011/0145096 A1 | * | 6/2011 | Jensen | 705/27.1 |
| 2011/0252890 A1 | * | 10/2011 | Matsuda | 73/632 |
| 2011/0263982 A1 | * | 10/2011 | Kano | 600/443 |
| 2012/0188849 A1 | * | 7/2012 | Matsuda et al. | 367/135 |
| 2014/0104989 A1 | * | 4/2014 | Matsuda | G01N 29/0654 367/138 |
| 2014/0116147 A1 | * | 5/2014 | Endo | G01H 11/08 73/658 |
| 2014/0116148 A1 | * | 5/2014 | Endo | G01H 11/08 73/661 |

FOREIGN PATENT DOCUMENTS

| | | |
|---|---|---|
| JP | 2007-142555 A | 6/2007 |
| JP | 2011-234073 A | 11/2011 |
| WO | 2009/008282 A1 | 1/2009 |

* cited by examiner

*Primary Examiner* — Long V Le
*Assistant Examiner* — Bradley Impink
(74) *Attorney, Agent, or Firm* — Global IP Counselors, LLP

(57) ABSTRACT

An ultrasonic device includes an ultrasonic element group, a first to an Nth driving electrode lines, first and second terminals. The ultrasonic element group includes a plurality of ultrasonic elements forming "N" columns arranged along a second direction intersecting with a first direction with each of the "N" columns including a plurality of the ultrasonic elements arranged along the first direction, "N" being a natural number that is equal to or more than 2. The first to the Nth driving electrode lines are arranged along the first direction. An ith driving electrode line is connected to the ultrasonic elements constituting an ith column among the "N" columns, with "i" being a natural number equal to or less than "N". The first terminal is connected to one end of the ith driving electrode line, and the second terminal is connected to the other end of the ith driving electrode line.

17 Claims, 18 Drawing Sheets

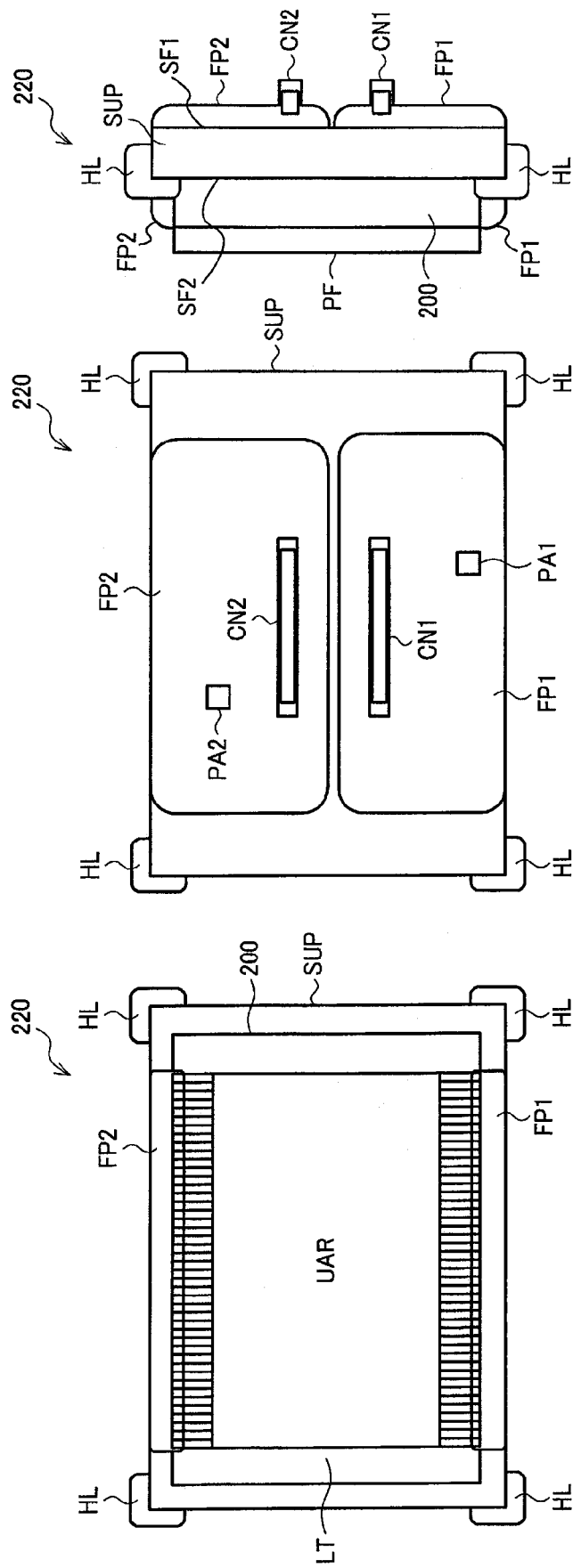

ULTRASONIC DEVICE, PROBE, ELECTRONIC INSTRUMENT, DIAGNOSTIC DEVICE, AND PROCESSING DEVICE

CROSS-REFERENCE TO RELATED APPLICATIONS

This application claims priority to Japanese Patent Application No. 2012-038360 filed on Feb. 24, 2012. The entire disclosure of Japanese Patent Application No. 2012-038360 is hereby incorporated herein by reference.

BACKGROUND

1. Technical Field

The present invention relates to an ultrasonic device, a probe, an electronic instrument, a diagnostic device, and a processing device.

2. Related Art

An ultrasonic device (for example, Japanese Laid-Open Patent Publication No. 2007-142555) has been known in which ultrasonic waves are emitted from a tip end of a probe toward a target and ultrasonic waves reflected on the target are detected. For example, this device is used as an ultrasonic diagnostic device in which the inside of a patient's body is imaged to be used for diagnosis. Generally, a piezoelectric element is used as an ultrasonic element that emits ultrasonic waves.

SUMMARY

A case of using a thin film piezoelectric element as an ultrasonic element will be considered. Piezoelectric elements are arranged in one line, a driving electrode line is arranged along the line of the piezoelectric elements, and a driving voltage is input from one end of the driving electrode line. In such a one-sided voltage application method, it turned out that a voltage drop occurs with respect to a voltage applied to a piezoelectric element at the other end to which a driving voltage is not applied compared to a voltage applied to a piezoelectric element that is close to the one end to which a driving voltage is applied. It is considered that this is because an RC distributed constant circuit is formed by the piezoelectric elements and the wiring. There is a problem that the radiated sound pressure distribution of ultrasonic waves is unevenly located on the side to which a driving voltage is applied due to such a voltage drop.

According to some aspects of the present invention, an ultrasonic device in which the radiated sound pressure distribution of ultrasonic waves is prevented from being unevenly located, a probe, an electronic instrument, a diagnostic device, a processing device, and the like can be provided.

According to one aspect of the present invention, an ultrasonic device includes an ultrasonic element group, a first to an Nth driving electrode lines, a first terminal and a second terminal. The ultrasonic element group includes a plurality of ultrasonic elements, the ultrasonic elements forming "N" columns arranged along a second direction intersecting with a first direction with each of the "N" columns including a plurality of the ultrasonic elements arranged along the first direction, "N" being a natural number that is equal to or more than 2. The first to the Nth driving electrode lines are arranged along the first direction. An ith driving electrode line among the first to the Nth driving electrode lines is connected to the ultrasonic elements constituting an ith column among the "N" columns, with "i" being a natural number that is equal to or less than "N". The first terminal is connected to one end of the ith driving electrode line, and the second terminal is connected to the other end of the ith driving electrode line.

With this aspect, a driving signal for driving the group of ultrasonic elements can be input to the first terminal provided at one end of the driving electrode line and the second terminal provided at the other end. It is thus possible to prevent the radiated sound pressure distribution of ultrasonic waves from being unevenly located.

According to one aspect of the present invention, a "M" number of the ultrasonic elements arranged in each column is preferably equal to or less than "m", with "m" being a natural number that is equal to or more than 3.

The sound pressure of the center of the column of ultrasonic elements at a predetermined depth is decreased when the number "M" passes the number in which the sound pressure becomes maximum even if the number "M" is increased. It is thus possible to save the area of the ultrasonic element array (the number of the elements) while obtaining a large sound pressure by setting the upper limit of the number "M" to be "m".

According to one aspect of the present invention, a number "M" is preferably equal to or less than "m" that is equal to "a", "a" being a number of the ultrasonic elements arranged in the first direction, with "a" being a natural number that is equal to or more than 3, when a sound pressure of a center of each column of the ultrasonic elements is half of a peak value with respect to sound pressure distribution characteristics in the first direction of ultrasonic waves output from the ultrasonic element group when a driving signal for driving the ultrasonic element group is input only to the first terminal.

With this aspect, since the upper limit of the number "M" is set to be m=a, the sound pressure distribution characteristics of ultrasonic waves are allowed to converge to the center of the column of ultrasonic elements in a case where a driving signal is supplied to both ends of the column of ultrasonic elements.

According to one aspect of the present invention, a number "M" is preferably equal to or less than "m" that is equal to "b", when sound pressure distribution characteristics in the first direction of ultrasonic waves output from the ultrasonic element group have double peaks when the number of the ultrasonic elements arranged in the first direction is b+1, with "b" being a natural number that is equal to or more than 3, and have a single peak when the number of the ultrasonic elements arranged in the first direction is "b" when a driving signal is input to the first terminal and the second terminal.

With this aspect, a maximum number M=b that maintains a single peak in a case of increasing the number "M" can be set to be a maximum value "m" of the number "M". Consequently, a single peak can be achieved with respect to the sound pressure distribution characteristics at a predetermined depth.

According to one aspect of the present invention, the ultrasonic device preferably further includes a driving signal output circuit configured to output a driving signal for driving the ultrasonic element group to the first terminal and the second terminal.

According to one aspect of the present invention, the driving signal output circuit is preferably configured to output the driving signal having different amplitude to the first terminal and the second terminal.

With this aspect, by outputting the driving signal having different amplitude to the first terminal and the second terminal, the peak position of an ultrasonic beam can be shifted to a side of the first terminal or a side of the second terminal of the column of ultrasonic elements.

According to one aspect of the present invention, the driving signal output circuit preferably has an output amplifier, a first variable resistance for adjusting amplitude of the driving signal to the first terminal provided between the output amplifier and the first terminal, and a second variable resistance for adjusting amplitude of the driving signal to the second terminal provided between the output amplifier and the second terminal.

With this aspect, by adjusting the resistance values of the first variable resistance and the second variable resistance, it becomes possible to output the driving signal having different amplitude to the first terminal and the second terminal.

According to one aspect of the present invention, a number of the ultrasonic elements arranged in each column is preferably "M", with "M" being a natural number that is equal to or more than 2, and the ultrasonic element group is a group of the ultrasonic elements arranged in a matrix pattern having "M" rows and the "N" columns in which the "N" columns of the ultrasonic elements are arranged.

With this aspect, the group of ultrasonic elements can be arranged in a matrix pattern having "M" rows and "N" columns. According to one aspect of the present invention, the arrangement of the group of ultrasonic elements is not limited to a matrix pattern, and a zigzag pattern may be possible, for example.

According to one aspect of the present invention, the ultrasonic device preferably further includes a plurality of common electrode lines that are arranged along the second direction.

With this aspect, by arranging the plurality of common electrode lines, the driving electrode lines and the common electrode lines can be insulated by the ultrasonic elements. Consequently, there is no need to provide an insulating layer for insulating the driving electrode lines and the common electrode lines other than the ultrasonic elements.

According to one aspect of the present invention, the ultrasonic device preferably further includes a shared common electrode line connected to the common electrode lines in common and arranged along the first direction.

According to one aspect of the present invention, the ultrasonic device preferably further includes terminals provided at both ends of the shared common electrode line for supplying a common voltage to the ultrasonic element group.

With this aspect, by connecting the plurality of common electrode lines to the shared common electrode line, a common voltage can be supplied from the shared common electrode line. Also, a common voltage can be supplied from the terminals in common with respect to the plurality of common electrode lines.

According to another aspect of the present invention, an ultrasonic device includes an ultrasonic element column in which a plurality of ultrasonic elements are arranged, a driving electrode line connected to the ultrasonic elements, a first terminal connected to one end of the driving electrode line, and a second terminal connected to the other end of the driving electrode line.

According to yet another aspect of the present invention, an ultrasonic device includes a column of ultrasonic elements in which a plurality of ultrasonic elements are arranged, and a driving electrode line connected to the plurality of ultrasonic elements. A driving signal for driving the plurality of ultrasonic elements is supplied to both ends of the driving electrode line.

According to yet another aspect of the present invention, there is provided a probe that includes the above-described ultrasonic device.

According to yet another aspect of the present invention, there is provided an electronic instrument that includes the above-described ultrasonic device.

According to yet another aspect of the present invention, there is provided a diagnostic device that includes the above-described ultrasonic device.

According to yet another aspect of the present invention, there is provided a processing device that includes the above-described ultrasonic device and a driving signal output circuit configured to output a driving signal to the first terminal and the second terminal of the ultrasonic device.

BRIEF DESCRIPTION OF THE DRAWINGS

Referring now to the attached drawings which form a part of this original disclosure:

FIG. 16A, FIG. 16B, and FIG. 16C show the details of the configuration example of the head unit.

DETAILED DESCRIPTION OF EXEMPLARY EMBODIMENTS

Next, preferred embodiments of the present invention will be explained in detail. The embodiments explained below shall not be construed as unreasonably limiting the subject matter of the present invention described in the claims, and all the elements explained in the embodiments are not necessarily essential to the solving means of the present invention.

1. Comparative Example

Figure 1:
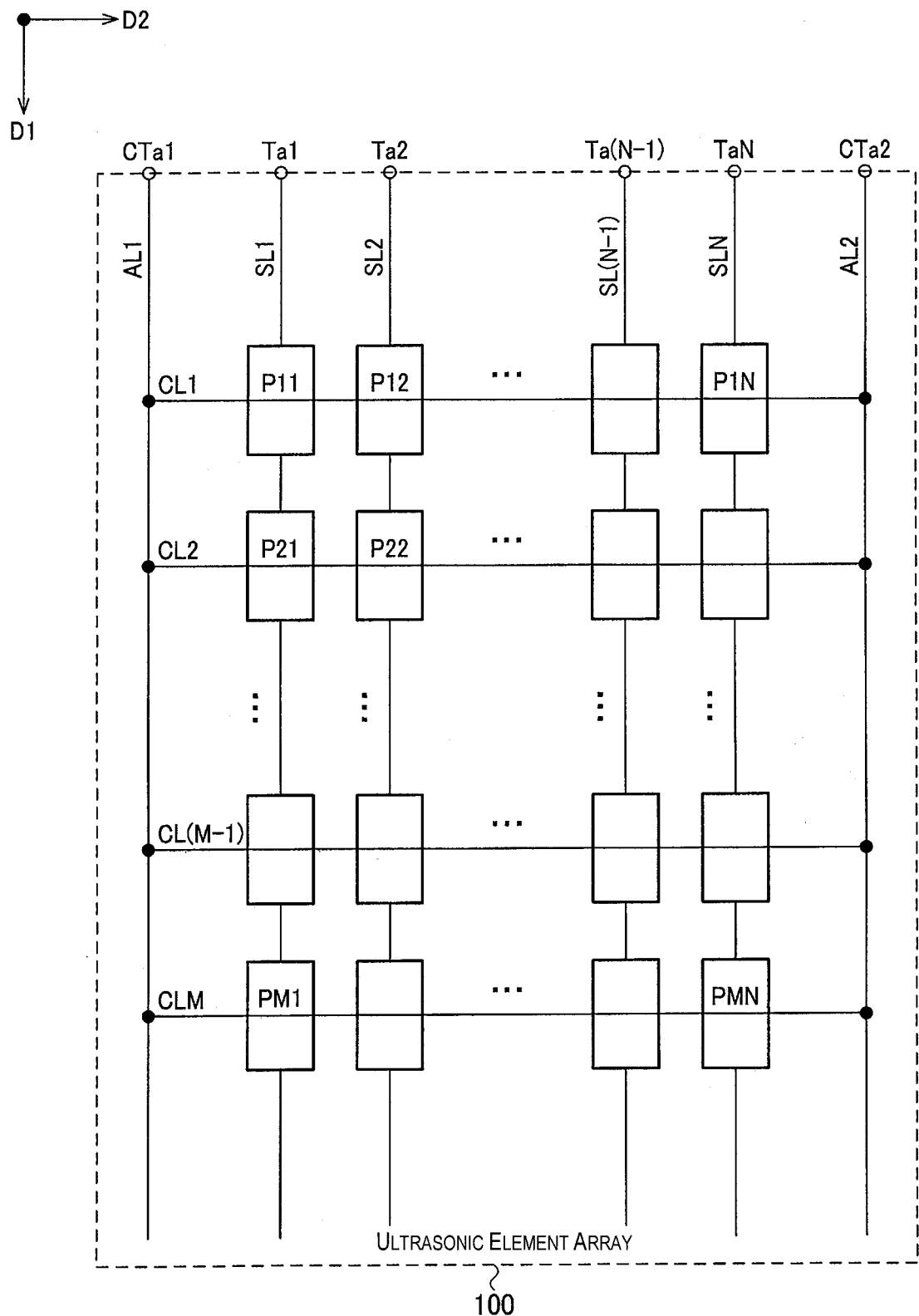
FIG. 1 shows an ultrasonic device according to a comparative example.

First, an ultrasonic device of a one-sided voltage application method will be explained as a comparative example of the present embodiment. FIG. 1 shows the ultrasonic device according to the comparative example.

The ultrasonic device shown in FIG. 1 includes an ultrasonic element array 100. The ultrasonic element array 100 includes driving terminals Ta1-TaN ("N" is a natural number that is equal to or more than 2) to which a driving voltage is supplied, a phase being controlled in the driving voltage to conduct phase scanning, driving electrode lines SL1-SLN connected to the driving terminals Ta1-TaN, thin film piezoelectric elements Pl1-PMN ("M" is a natural number that is equal to or more than 2), common terminals CTa1, CTa2 to which a common voltage is supplied, shared common electrode lines AL1, AL2 connected to the common terminals CTa1, CTa2, and common electrode lines CL1-CLM connected to the shared common electrode lines AL1, AL2.

Hereinafter, for simplicity, an $i^{th}$ column of thin film piezoelectric elements Pli-PMi ("i" is a natural number that is equal to or less than "N") among the thin film piezoelectric elements Pl1-PMN will be explained as an example.

The driving electrode line SLi is connected to one of electrodes of the thin film piezoelectric elements Pli-PMi, and a driving voltage supplied to the driving terminals Tai is applied thereto. The driving voltage is an alternating voltage having the same frequency as emitted ultrasonic waves. The common electrode lines CL1-CLM are connected to the other electrode, and a common voltage supplied to the common terminals CTa1, CTa2 is applied thereto. The common voltage is a predetermined direct voltage.

In this comparative example, the driving voltage is supplied only from one end of the driving electrode line SLi to which the driving terminal Tai is connected. In such a one-sided voltage application method, the amplitude of an applied voltage becomes smaller (a voltage drop occurs) in a thin film piezoelectric element that is farther away from the terminal Tai compared to the amplitude of a voltage applied to the thin film piezoelectric elements Pli that is close to the terminal Tai. This is because a parasitic capacitance appears between the electrodes of the thin film piezoelectric elements that have a structure in which a driving electrode and a common electrode are provided in both surfaces of the thin film piezoelectric element. In other words, this is because an RC distributed constant circuit is formed by the parasitic capacitance and the wiring resistance and the other end of the driving electrode line SLi is in a floating state.

Figure 2:
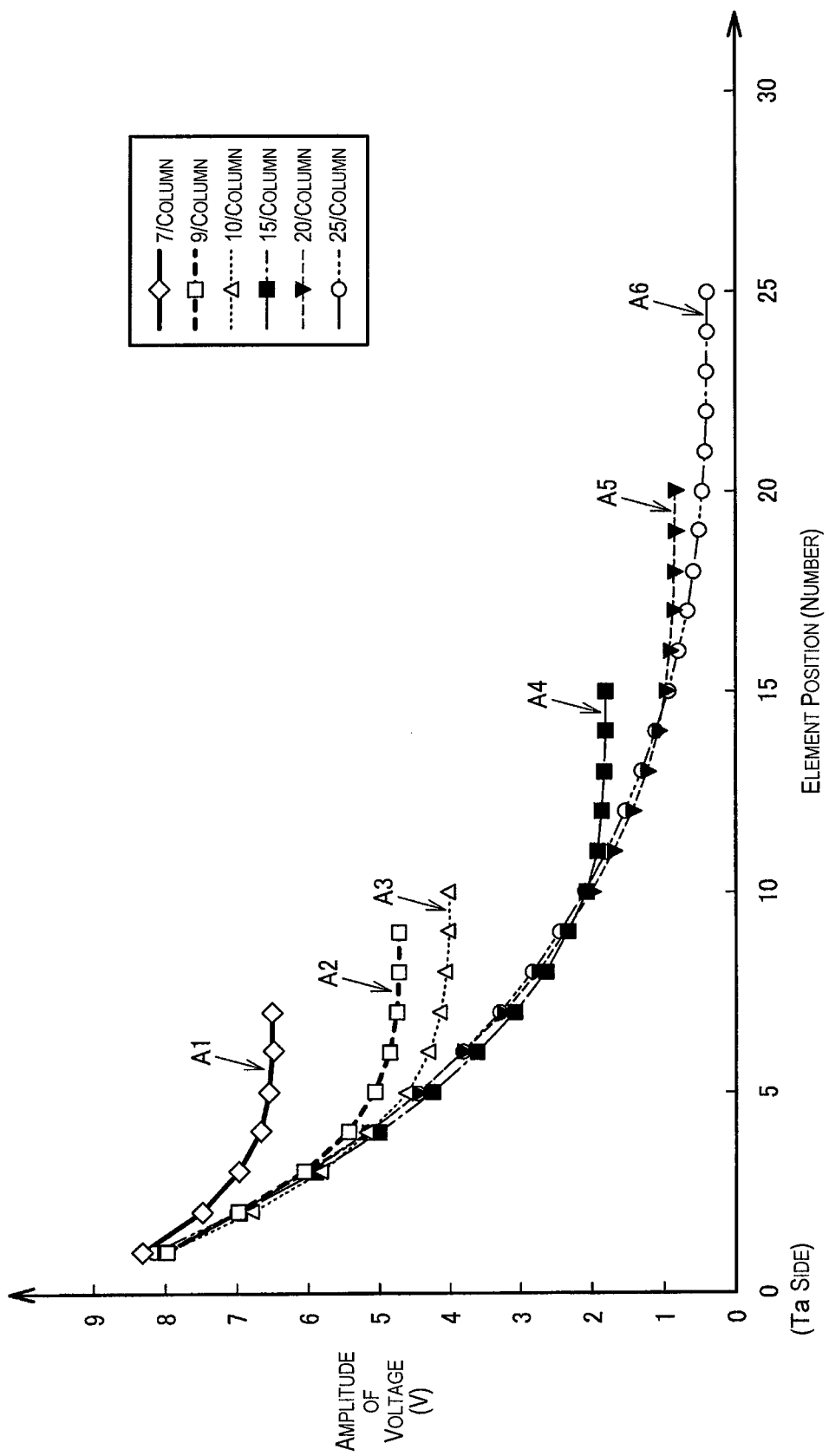
FIG. 2 shows an example of characteristics of the amplitude of a voltage applied between electrodes of thin film piezoelectric elements in the ultrasonic device according to the comparative example.

FIG. 2 shows an example of characteristics of the amplitude of a voltage applied between the electrodes of the thin film piezoelectric elements in the one-sided voltage application method. In FIG. 2, the parasitic capacitance of the thin film piezoelectric element and the parasitic resistances of the driving electrode line and the common electrode line are modeled, and the simulation results in a case of supplying a driving voltage from the driving terminal Tai on one side of the driving electrode line SLi. A1-A6 of FIG. 2 show examples of characteristics of the amplitude of a voltage applied between the electrodes of the thin film piezoelectric elements when the number "M" of the thin film piezoelectric elements Pli-PMi is 7, 9, 10, 15, 20, or 25, respectively. The element position in the horizontal axis indicates what number from the driving terminal Tai side the thin film piezoelectric element is.

As shown in A1-A6, the amplitude of a driving voltage applied between the electrodes becomes smaller in a thin film piezoelectric element that is farther away from the driving terminal Tai. The drop of the voltage amplitude becomes more significant in the same element position as the number of the thin film piezoelectric elements increases. When the amplitude of a voltage applied between the electrodes becomes small, the displacement amount of the thin film piezoelectric element becomes small proportionately, and thus the sound pressure radiated from the thin film piezoelectric element becomes small. Consequently, the radiated sound pressure of ultrasonic waves becomes smaller as it gets farther away from the driving terminal Tai, and the radiated sound pressure distribution is unevenly located on the side of the driving terminal Tai. Also, the sound pressure in the center (the sound pressure in the element position M/2) is decreased. The unevenness and the decrease in the sound pressure become more significant as the frequency becomes high.

Figure 3A:
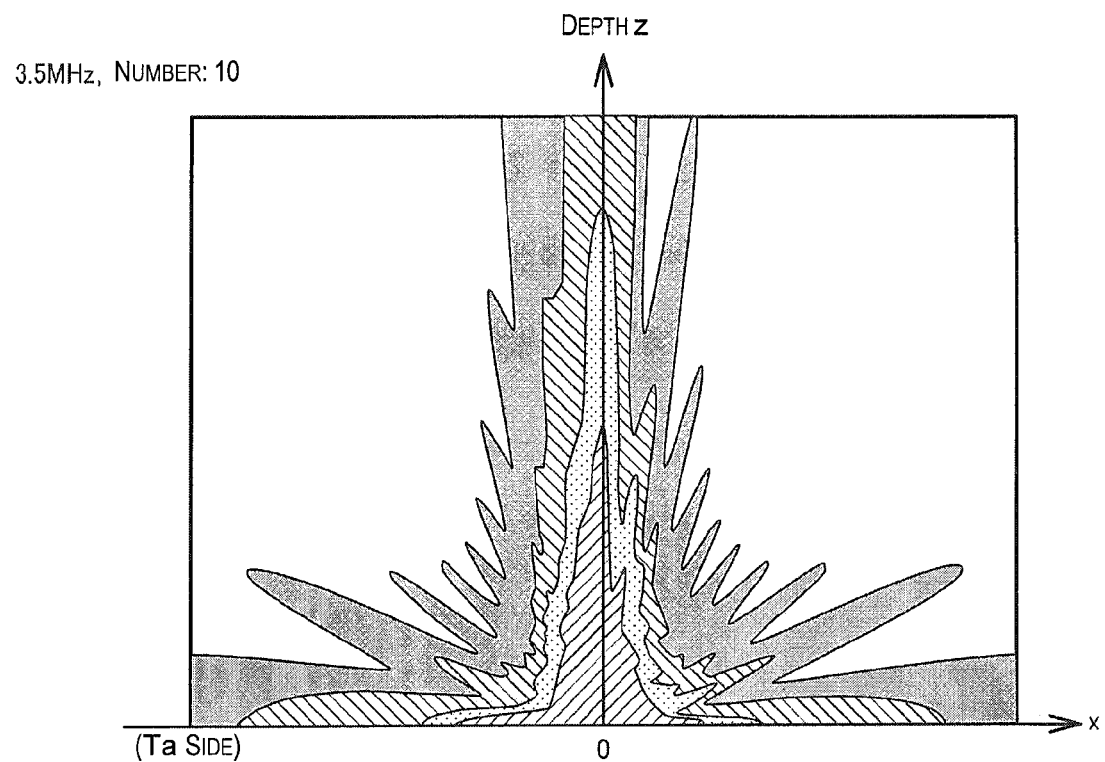
FIG. 3A and FIG. 3B show simulation results of sound pressure distribution characteristics in the ultrasonic device according to the comparative example.

FIG. 3A to FIG. 5B show simulation results of sound pressure distribution characteristics when the frequency of a driving voltage is 3.5 MHz in a one-sided voltage application method. In FIG. 3A to FIG. 5B, the x-axis shows a position in a direction along the column of the elements (a direction parallel to D1 in FIG. 1). The ultrasonic device of FIG. 1 is placed in the position of x=0. The negative side is the side of the driving terminal Tai. In FIG. 3A, FIG. 4A, and FIG. 5A, the z-axis shows a depth, and the sound pressure distribution is shown by lines of equal sound pressure. The depth refers to a position in an emission direction of ultrasonic waves, that is, a position in a direction along a normal line of a plane from which ultrasonic waves are emitted in the ultrasonic element array.

Figure 3B:
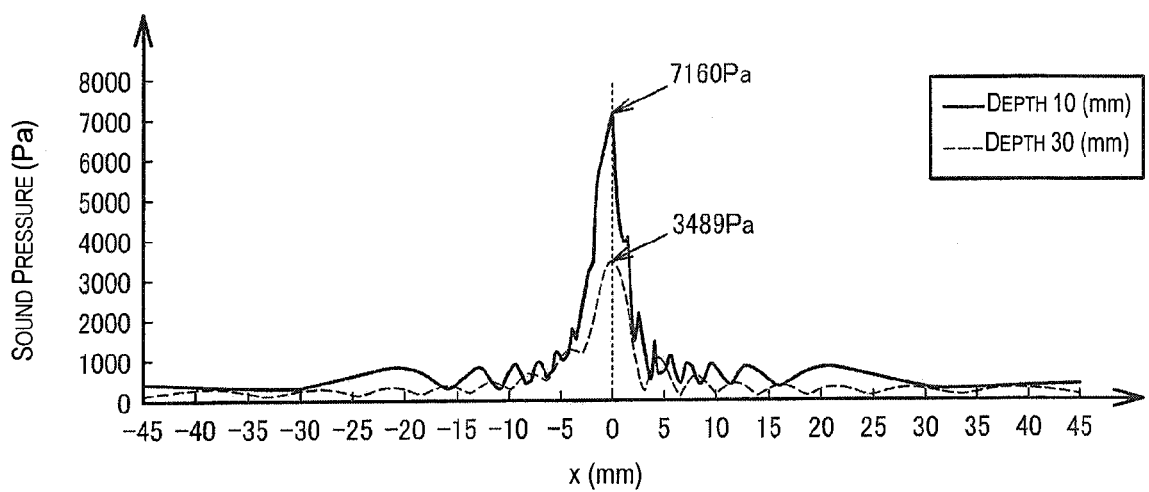
Figure 4A:
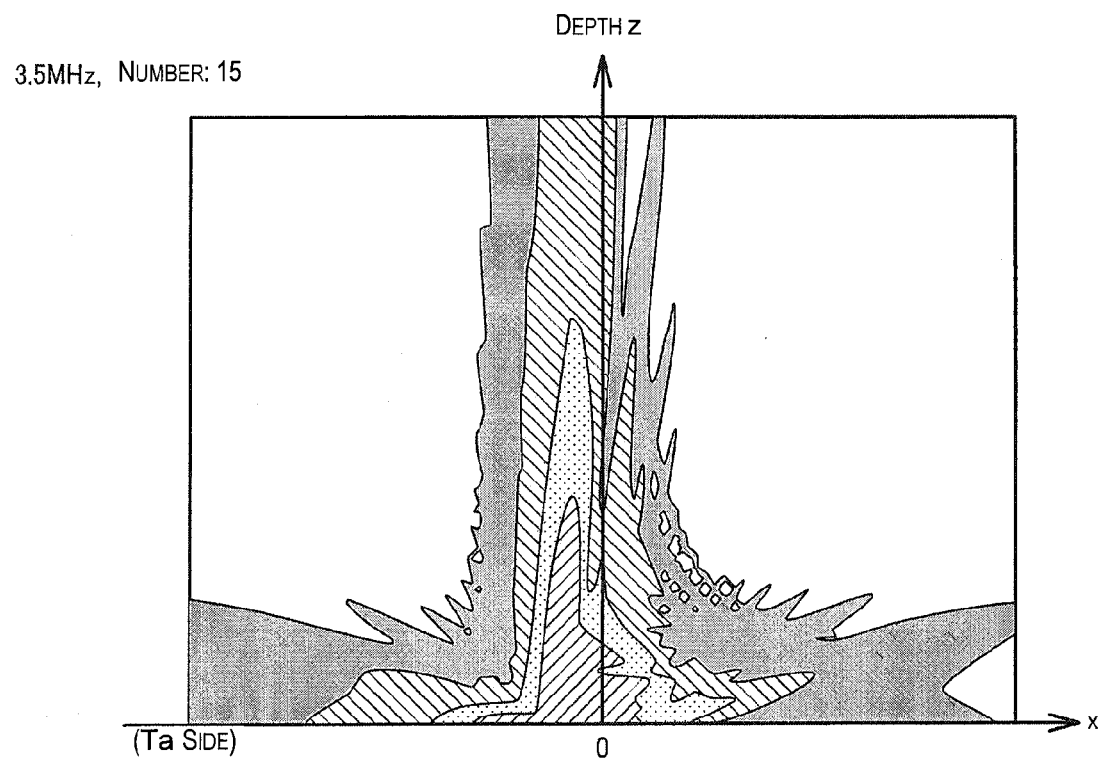
FIG. 4A and FIG. 4B show simulation results of sound pressure distribution characteristics in the ultrasonic device according to the comparative example.
Figure 4B:
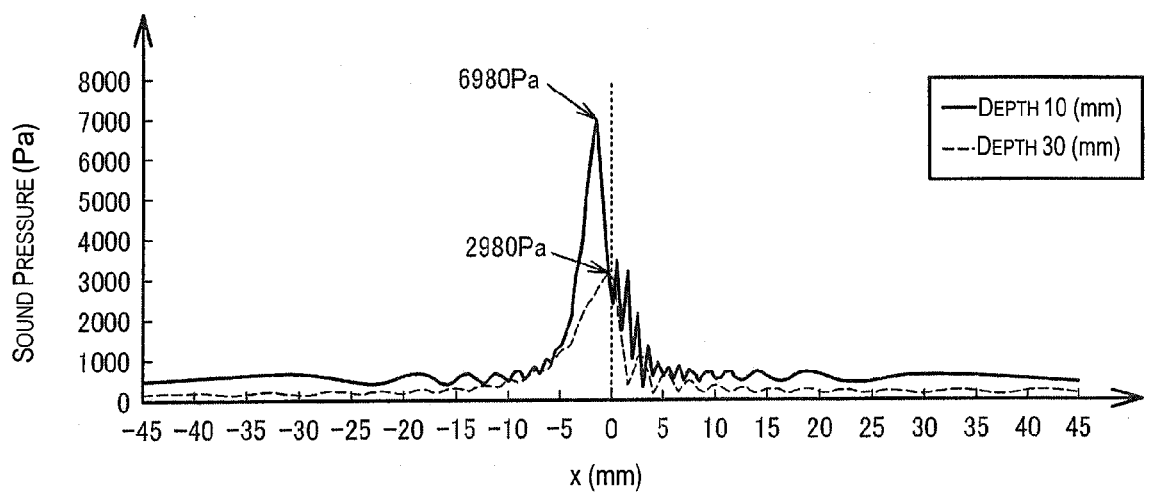
Figure 5A:
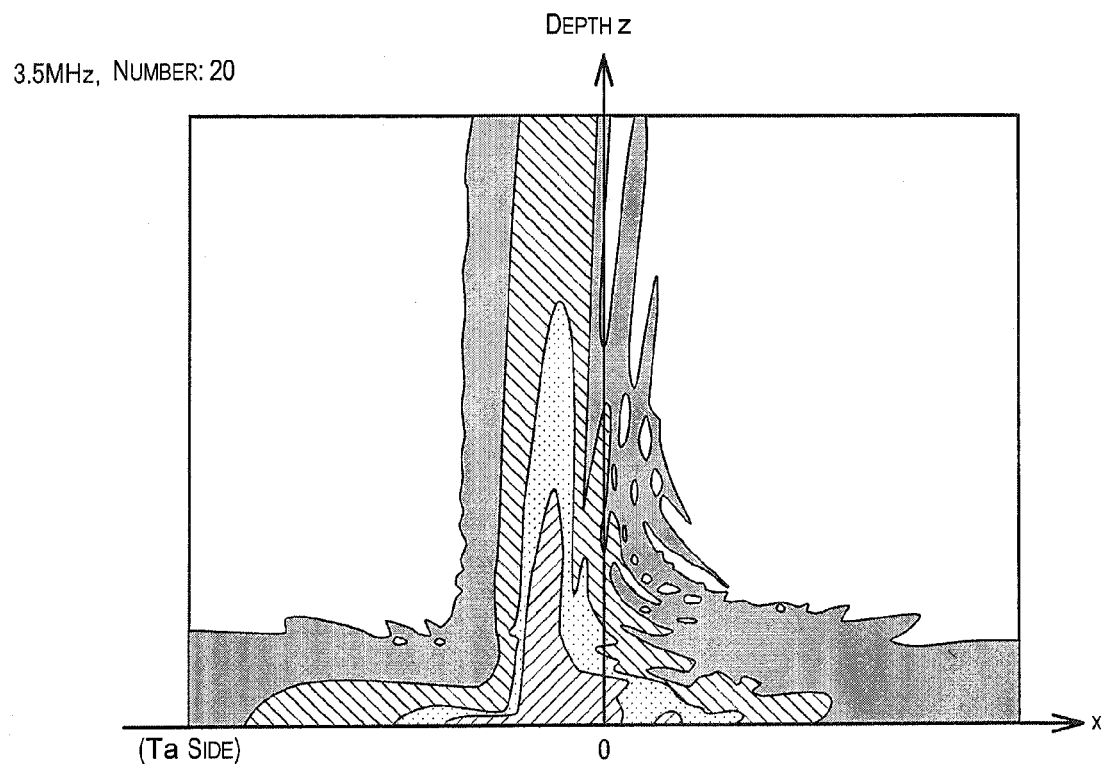
FIG. 5A and FIG. 5B show simulation results of sound pressure distribution characteristics in the ultrasonic device according to the comparative example.
Figure 5B:
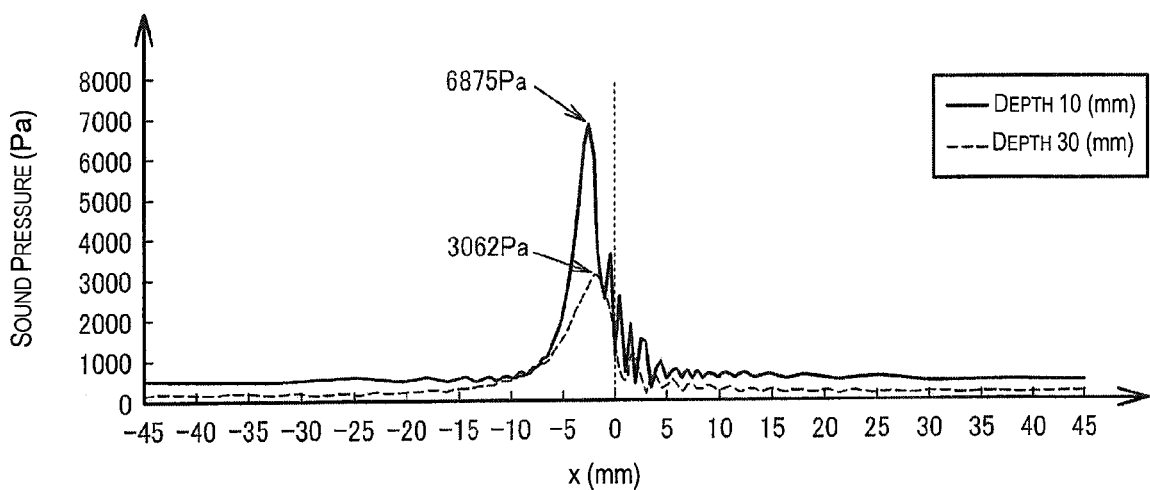

FIG. 3A and FIG. 3B show an example of sound pressure distribution characteristics when the number "M" of the elements in a column is 10. FIG. 4A and FIG. 4B show an example of sound pressure distribution characteristics when the number "M" of the elements in a column is 15. FIG. 5A and FIG. 5B show an example of sound pressure distribution characteristics when the number "M" of the elements in a column is 20.

As can be seen from these sound pressure distributions, the peak of ultrasonic beams in which the sound pressure becomes maximum is unevenly located on the side of the driving terminal Tai, and the unevenness becomes larger as the number "M" of the elements increases. For example, as shown in FIG. 3A, FIG. 4A, and FIG. 5A, the lines of equal sound pressure of the ultrasonic beams are asymmetrical with respect to x=0, and the asymmetricity becomes larger as the number "M" of the elements increases. Further, as shown in FIG. 4B, the peak of the sound pressure at a depth of 30 mm is located in x=-1.5 mm when M is 15, and as shown in FIG. 5B, the peak of the sound pressure at a depth of 30 mm is located in x=-2.5 mm when M is 20. As the number "M" of the elements increases, the peak of the sound pressure at a depth of 10 mm becomes more asymmetrical with respect to x=0, and the sound pressure on the terminal side becomes larger. As shown in FIG. 5B, the peak of the sound pressure at a depth of 10 mm is located in x=-1.5 mm when M is 20.

The sound pressure in the center x=0 of the element column becomes smaller as the number "M" of the elements increases corresponding to the unevenness of the sound pressure distribution. In FIG. 3B, FIG. 4B, and FIG. 5B, the peak sound pressure of the sound pressure distribution is shown in numerical values. The peak sound pressure normally increases as the number "M" of the elements increases unless the amplitude of the voltage drops. However, when a voltage drop occurs due to the RC distributed constant circuit, the increase in the number "M" of the elements does not contribute to the sound pressure, and the peak sound pressure cannot be made larger even if the number "M" of the elements is increased.

2. Configuration Example of Ultrasonic Device in Present Embodiment

Figure 6:
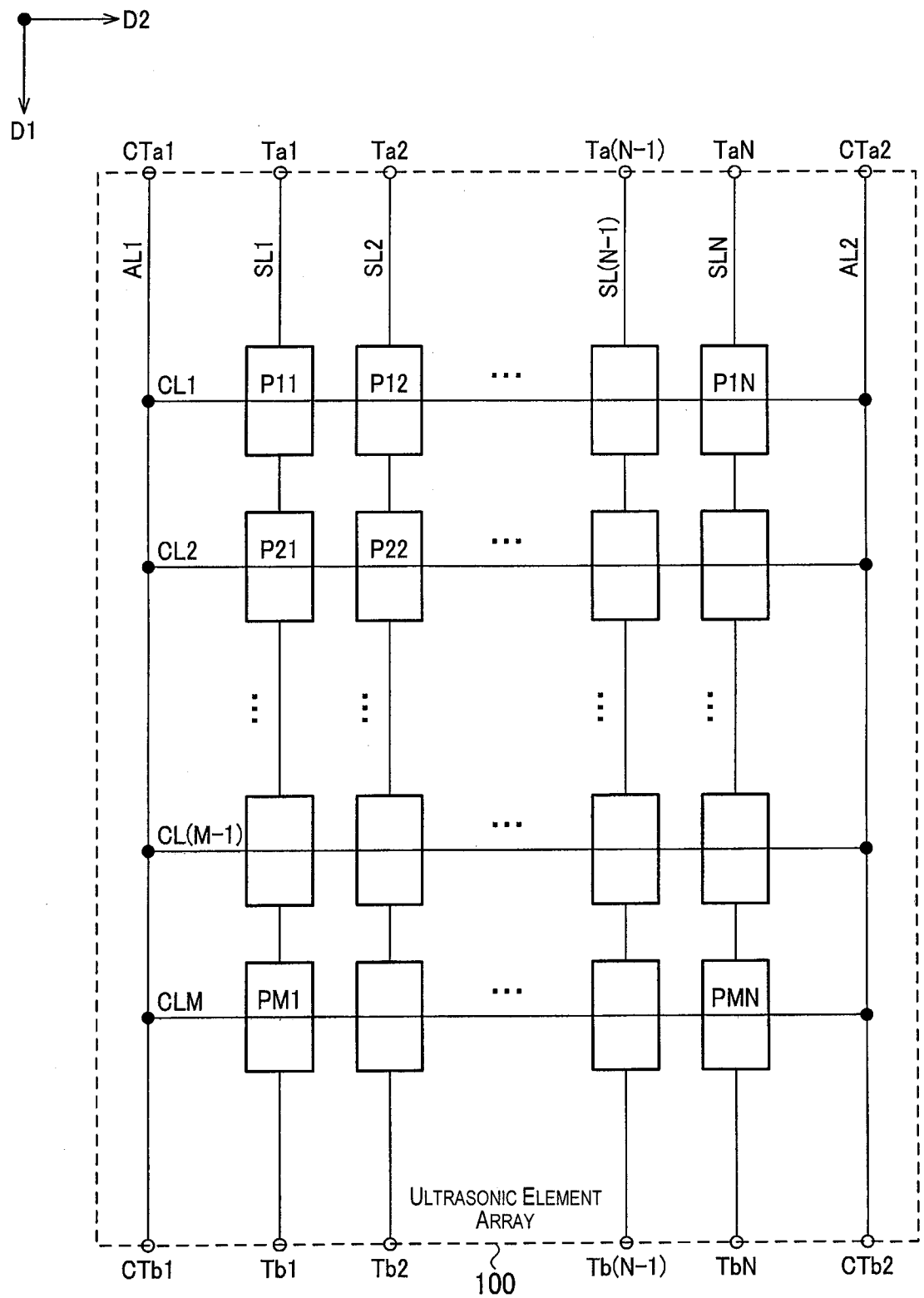
FIG. 6 shows a configuration example of an ultrasonic device according to the present embodiment.

FIG. 6 shows a configuration example of an ultrasonic device according to the present embodiment that can solve the problems such as the unevenness of the sound pressure distribution or the decrease in the sound pressure as described above. Hereinafter, a case where the ultrasonic element (ultrasonic transducer element in a narrow sense) is a thin film piezoelectric element (piezoelectric element) will be explained as an example. However, the present embodiment is not limited to this. Specifically, it is sufficient for the ultrasonic element to be an element that converts electric signals into ultrasonic waves, and it is sufficient if a parasitic capacitance exists between the electrodes of the ultrasonic elements. For example, a piezoelectric element that is not a thin film may be possible.

The ultrasonic device shown in FIG. 6 includes an ultrasonic element array 100. The ultrasonic element array 100 includes driving electrode lines SL1-SLN ("N" is a natural number that is equal to or more than 2), driving terminals Ta1-TaN connected to one end side of the driving electrode lines SL1-SLN, driving terminals Tb1-TbN connected to the other end side of the driving electrode lines SL1-SLN, a plurality of thin film piezoelectric elements Pl1-PMN (a plurality of ultrasonic elements in a broad sense) that constitute a group of ultrasonic elements, shared common electrode lines AL1, AL2, common terminals CTa1, CTa2 connected to one end side of the shared common electrode lines AL1, AL2, common terminals CTb1, CTb2 connected to the other end side of the shared common electrode lines AL1, AL2, and common electrode lines CL1-CLM connected to the shared common electrode lines AL1, AL2 ("M" is a natural number that is equal to or more than 2).

The plurality of thin film piezoelectric elements Pl1-PMN are two-dimensionally arranged in the ultrasonic element array 100. Specifically, in each column of the group of ultrasonic elements, "M" thin film piezoelectric elements are arranged along a first direction D1. In each row of the group of ultrasonic elements, "N" thin film piezoelectric elements are arranged along a second direction D2 that is orthogonal to (intersects with in a broad sense) the first direction D1. The thin film piezoelectric element is formed by layering the driving electrode line, the thin film piezoelectric element, and the common electrode line in this order, for example, on a silicon substrate. It is configured such that a driving electrode is provided on one surface of the thin film piezoelectric element and a common electrode is provided on the other surface of the thin film piezoelectric element. The electrode line is made of metal wiring, for example.

The present embodiment uses a two-sided voltage application method in which a driving voltage is supplied from both ends of the column of the elements. Specifically, a driving voltage (driving signal in a broad sense) from a driving voltage output circuit described below with reference to FIG. 12, for example, is supplied to the driving terminals Ta1-TaN and the driving terminals Tb1-TbN. An alternating voltage having the same amplitude and the same phase is input to terminals Tai, Tbi at both ends of the driving electrode line SLi ("i" is a natural number that is equal to or less than "N") as a driving voltage. A driving voltage in which a phase is controlled to conduct phase scanning is supplied to the driving terminals Ta1-TaN and the driving terminals Tb1-TbN. Specifically, the second direction D2 corresponds to a scanning direction in the phase scanning, and the first direction D1 corresponds to a slice direction. Incidentally, as described below with reference to FIG. 12, a driving voltage having different amplitude may be supplied to the terminals Tai, Tbi.

The driving electrode lines SL1-SLN are arranged along the first direction D1 and connected to the thin film piezoelectric elements of the corresponding columns. More specifically, the $i^{th}$ driving electrode line SLi among the driving electrode lines SL1-SLN is connected to the driving electrodes of the thin film piezoelectric elements Pli-PMi in the $i^{th}$ column.

The common electrode lines CL1-CLM are arranged along the second direction D2 and connected to the thin film piezoelectric elements of the corresponding rows. Specifically, the $j^{th}$ common electrode line CLj ("j" is a natural number that is equal to or more than 3, and is equal to or less than "M") among the common electrode lines CL1-CLM is connected to the common electrodes of the thin film piezoelectric elements Pj1-PjN in the $j^{th}$ row. One ends of the common electrode lines CL1-CLM are connected to the shared common electrode line AL1, and the other ends of the common electrode lines CL1-CLM are connected to the shared common electrode line AL2. A common voltage is supplied to the common electrode lines CL1-CLM through the common terminals CTa1, CTa2, CTb1, and CTb2. A direct voltage having the same voltage is supplied from a common voltage output circuit that is not shown in the drawing to the common terminals CTa1, CTa2, CTb1, and CTb2.

The ultrasonic device shown in FIG. 6 is formed as a one-chip integrated circuit device, for example. In such a case, the driving terminal and the common terminal correspond to the terminals of the chip. A driving voltage and a common voltage are supplied from the outside of the chip to the terminals. However, the present embodiment is not limited to this. The ultrasonic device may include a driving voltage output circuit (for example, driving voltage output circuit shown in FIG. 12) or a common voltage output circuit in addition to the configuration of FIG. 6. In such a case, the driving voltage output circuit and the common voltage output circuit are integrated into the integrated circuit device, and the driving terminal and the common terminal correspond to the terminals between the circuit blocks.

3. Example of Characteristics

Figure 7:
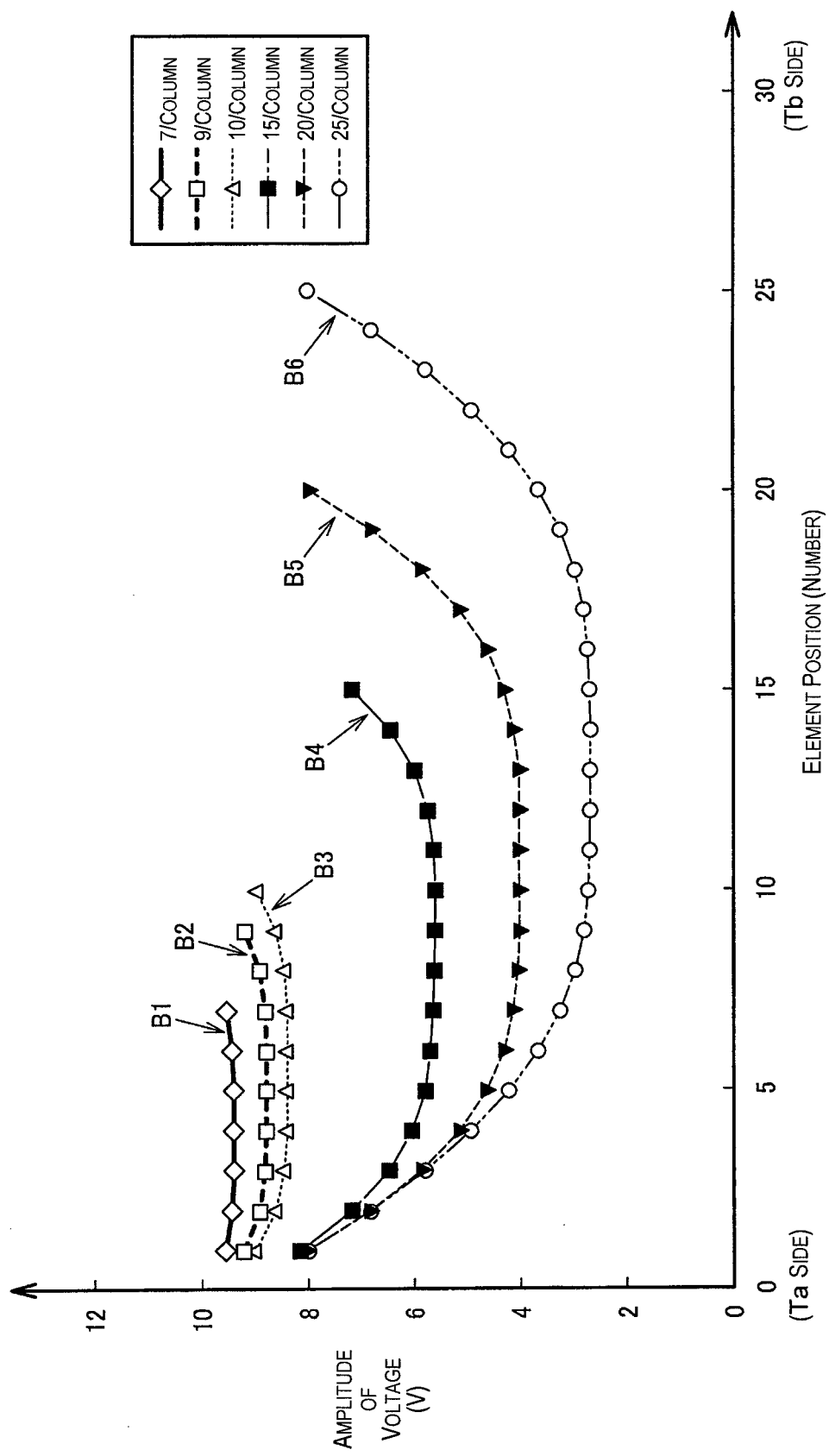
FIG. 7 shows an example of characteristics of the amplitude of a voltage applied between electrodes of thin film piezoelectric elements in the ultrasonic device according to the present embodiment.

FIG. 7 shows an example of characteristics of the amplitude of a voltage applied between the electrodes of the thin film piezoelectric elements in the present embodiment of the two-sided voltage application method. In FIG. 7, the parasitic capacitance of the thin film piezoelectric element and the parasitic resistances of the driving electrode line and the common electrode line are modeled, and the simulation results in a case of supplying a driving voltage from the terminals Tai, Tbi on both sides of the driving electrode line SLi. The driving voltage supplied to the terminals Tai, Tbi is the same as that of the comparative example, and the modeled parasitic capacitance and parasitic resistances are the same as those of the comparative example. B1-B6 of FIG. 7 show examples of characteristics of the amplitude of a voltage applied between the electrodes of the thin film piezoelectric elements when the number "M" of the thin film piezoelectric elements Pli-PMi is 7, 9, 10, 15, 20, or 25, respectively. The element position in the horizontal axis shows what number from the driving terminal Tai side the thin film piezoelectric element is.

As shown in B1-B6, the amplitude of a voltage applied between the electrodes of the thin film piezoelectric elements is the same on both ends of the column of the elements, which is different from the characteristics of the comparative example shown in FIG. 2 in which the amplitude of a voltage becomes smaller in a thin film piezoelectric element that is farther away from the terminal Tai. Although the amplitude of a voltage decreases as it gets closer to the center of the element column (the element position M/2), the decrease amount in the center of the element column is smaller than that of the comparative example shown in FIG. 2 (the amplitude of a voltage is large). In this manner, when a driving voltage is applied to both ends of the element column, the characteristics of the amplitude of a voltage applied between the electrodes of the thin film piezoelectric elements is symmetrical with respect to the center of the element column, and the decrease in the voltage amplitude is controlled. Therefore, the radiated sound pressure distribution of ultrasonic waves is symmetrical with respect to the center of the element column, and the radiated sound pressure is improved in the same number of elements and the same driving voltage compared to the comparative example. It can be thus expected that higher radiated sound pressure will be obtained in a smaller number of elements or a lower driving voltage than those of the comparative example of a one-sided voltage application method.

Figure 8A:
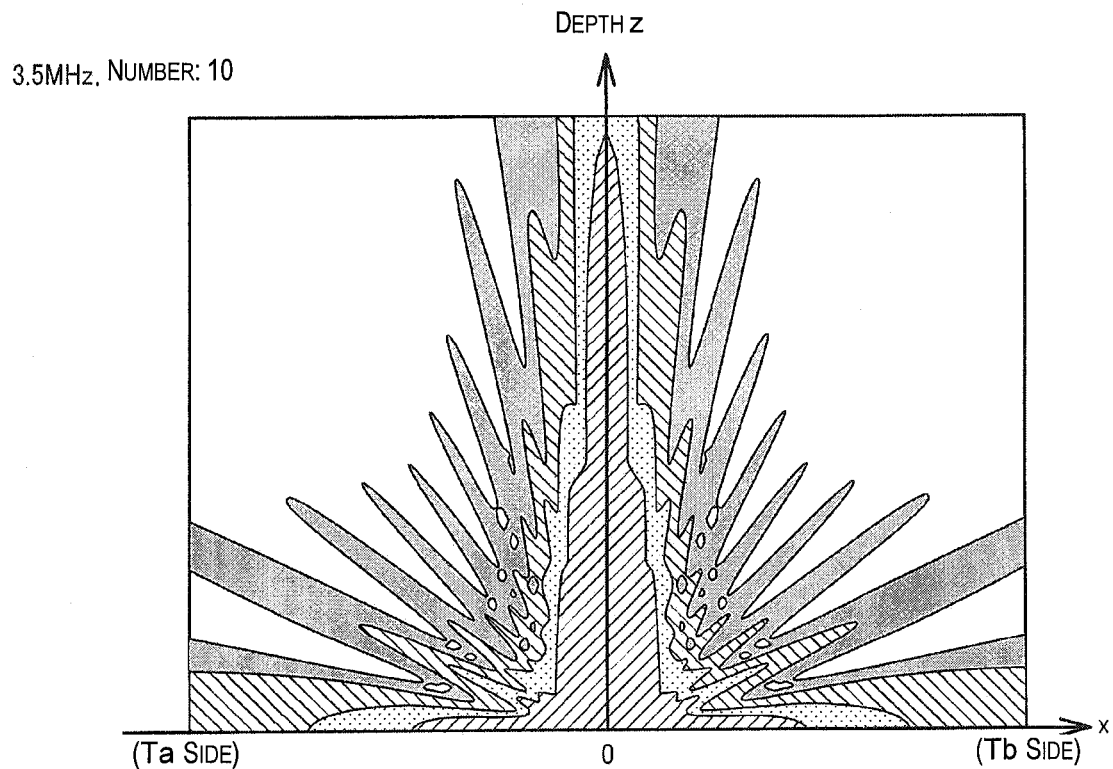
FIG. 8A and FIG. 8B show simulation results of sound pressure distribution characteristics in the ultrasonic device according to the present embodiment.

FIG. 8A to FIG. 10B show simulation results of sound pressure distribution characteristics when the frequency of a driving voltage is 3.5 MHz in the present embodiment of a two-sided voltage application method. The driving voltage supplied to the terminals Tai, Tbi is the same as that of the comparative example. In FIG. 8A to FIG. 10B, the x-axis shows a position in a direction along the column of the elements (a direction parallel to D1 in FIG. 6). The ultrasonic device of FIG. 6 is placed in the position of x=0. The negative side is the side of the driving terminal Tai. In FIG. 8A, FIG. 9A, and FIG. 10A, the z-axis shows a depth, and the sound pressure distribution is shown by lines of equal sound pressure. The depth refers to a position in an emission direction of ultrasonic waves that is orthogonal to the direction D1 and the direction D2 of FIG. 6.

Figure 8B:
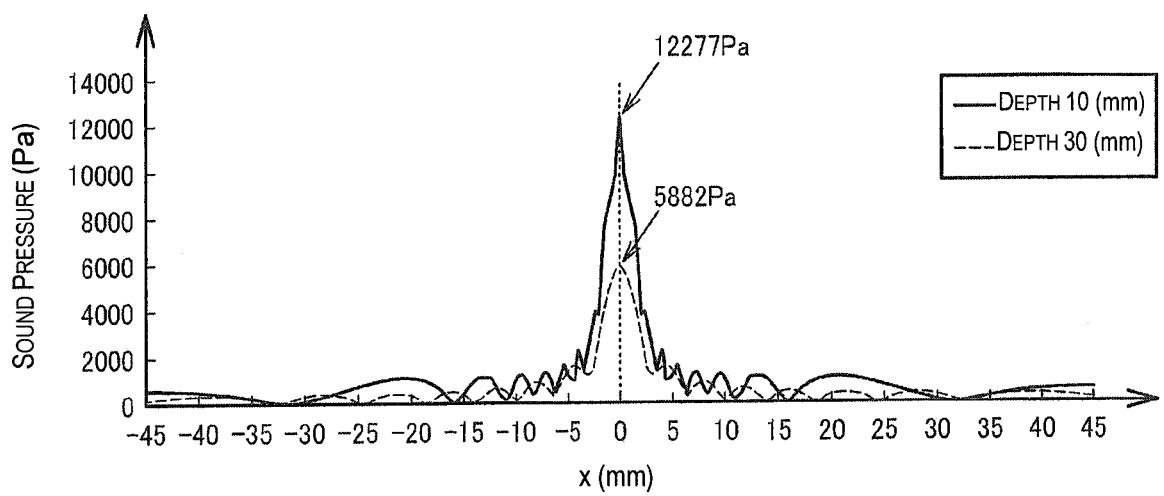
Figure 9A:
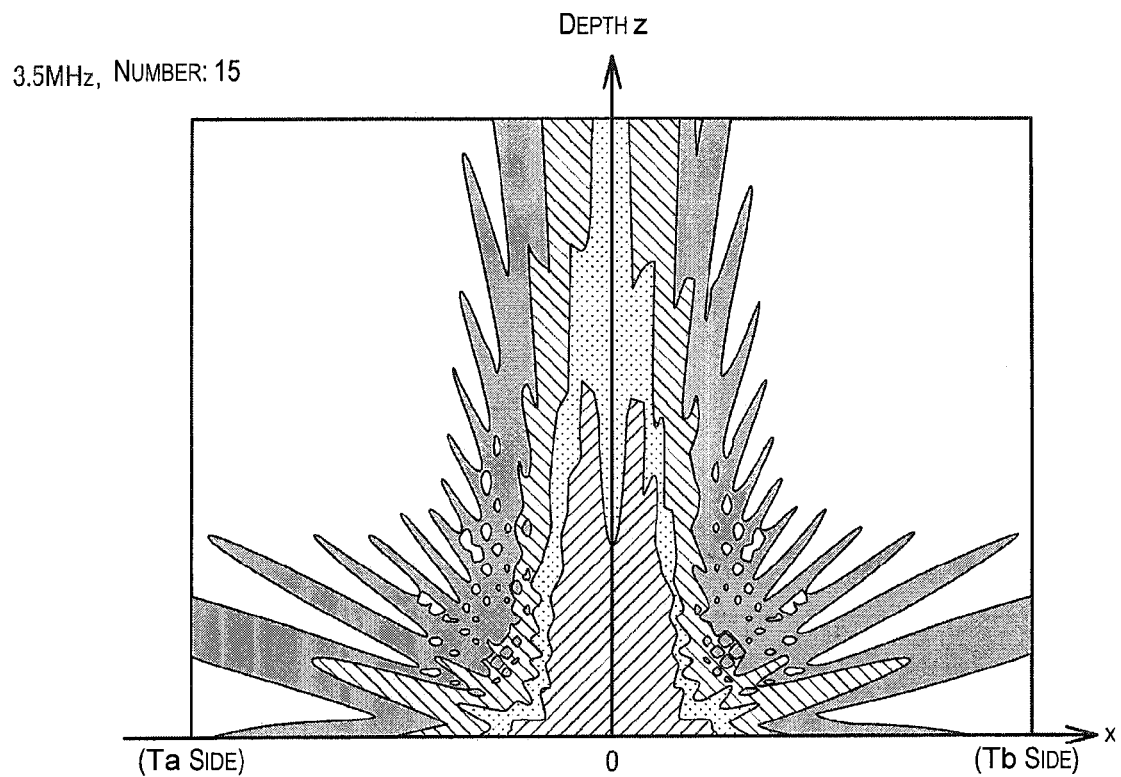
FIG. 9A and FIG. 9B show simulation results of sound pressure distribution characteristics in the ultrasonic device according to the present embodiment.
Figure 9B:
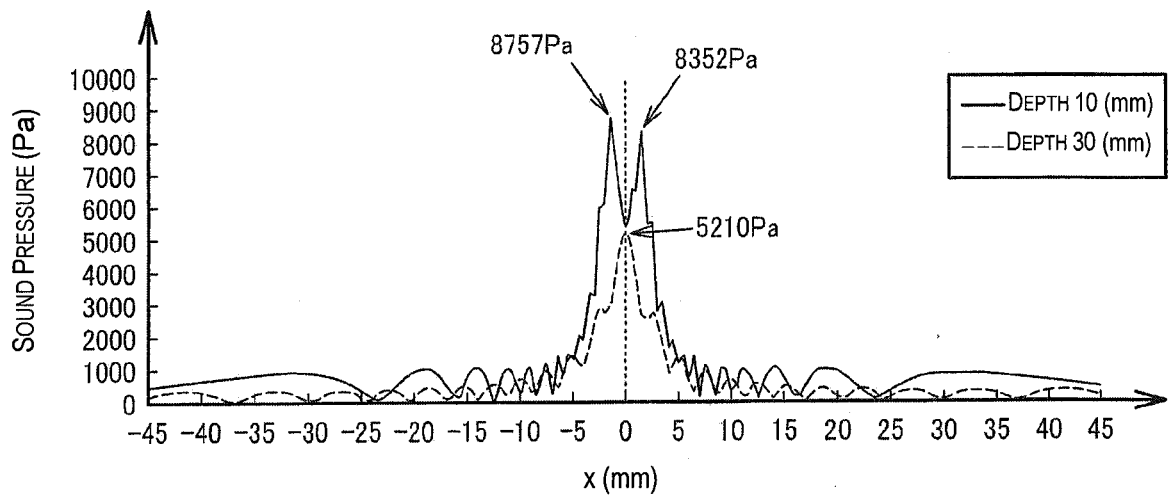
Figure 10A:
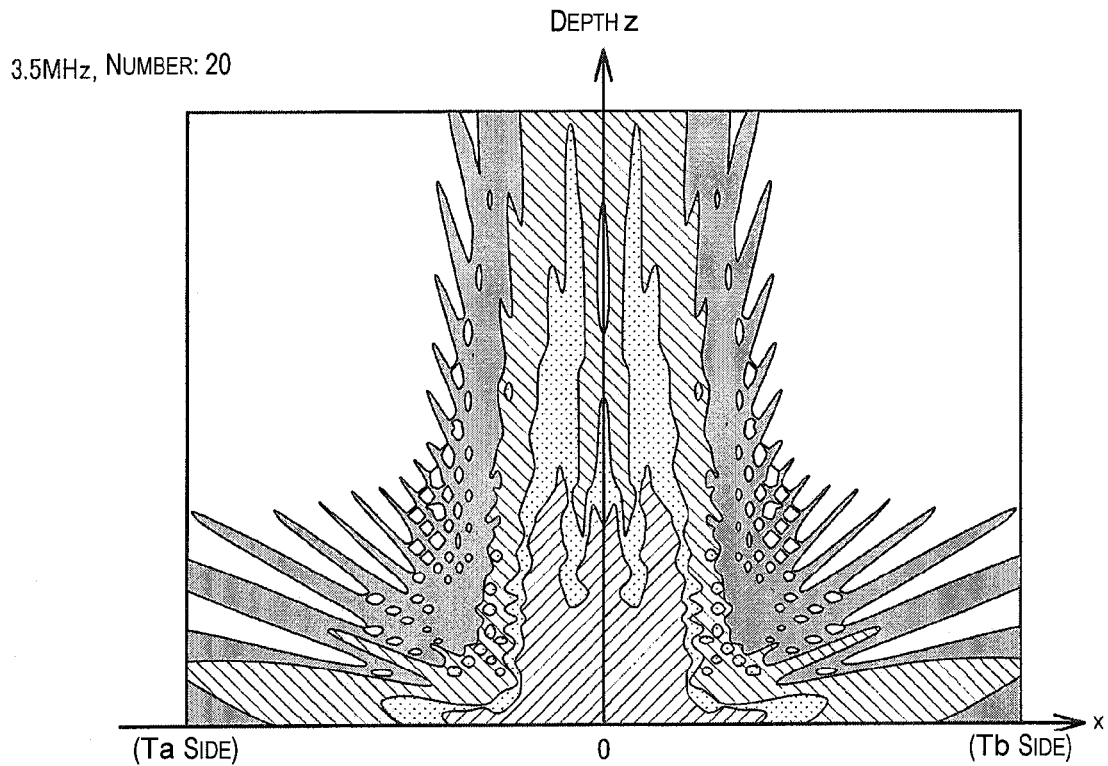
FIG. 10A and FIG. 10B show simulation results of sound pressure distribution characteristics in the ultrasonic device according to the present embodiment.
Figure 10B:
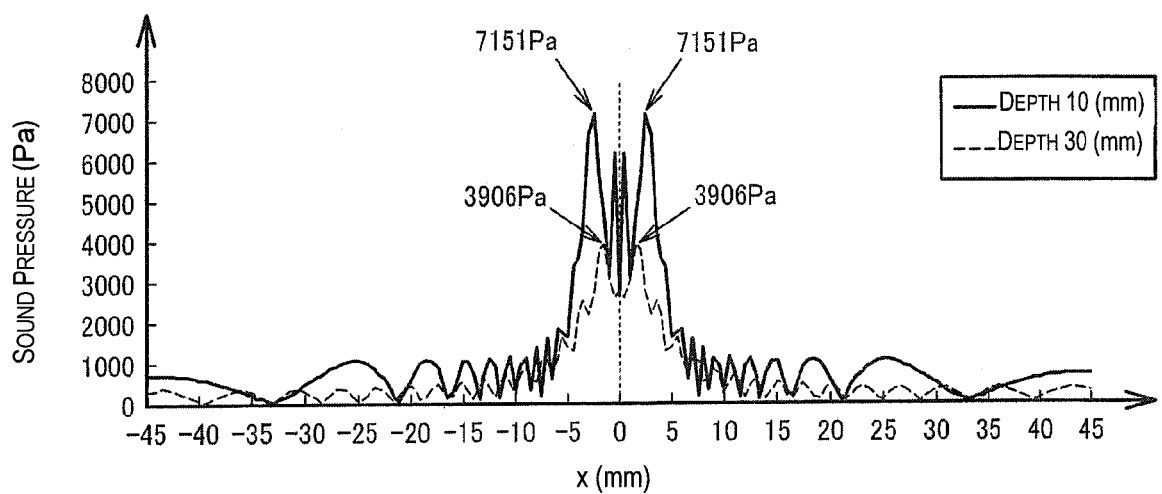

FIG. 8A and FIG. 8B show an example of sound pressure distribution characteristics when the number "M" of the elements in a column is 10. FIG. 9A and FIG. 9B show an example of sound pressure distribution characteristics when the number "M" of the elements in a column is 15. FIG. 10A and FIG. 10B show an example of sound pressure distribution characteristics when the number "M" of the elements in a column is 20.

As can be seen from these sound pressure distributions, the peak of ultrasonic beams in which the sound pressure becomes maximum is not unevenly located on either side of the driving terminals Tai, Tbi. For example, as shown in FIG. 8A, FIG. 9A, and FIG. 10A, the lines of equal sound pressure of the ultrasonic beams are symmetrical with respect to x=0. Further, as shown in FIG. 8B, the peak of the sound pressure at a depth of 30 mm is located in x=0 when M is 10. As shown in FIG. 9B, the peak of the sound pressure at a depth of 30 mm is located in x=+1.5 mm and x=−1.5 mm when M is 15. As shown in FIG. 10B, the peak of the sound pressure at a depth of 30 mm is located in x=+2.5 mm and x=−2.5 mm when M is 20. As shown in FIG. 8B and FIG. 9B, the peak of the sound pressure at a depth of 10 mm is located in x=0 when M is 10, 15. As shown in FIG. 10B, the peak of the sound pressure at a depth of 10 mm is located in x=+0.5 mm and x=−0.5 mm when M is 20.

When the comparative example of FIG. 3A to FIG. 5B and the present embodiment of FIG. 8A to FIG. 10B are compared, both of the peak value of the sound pressure and the sound pressure in the center x=0 of the element column are greater in the present embodiment than in the comparative example with respect to any number "M" of the elements. By using a two-sided voltage application method, it is possible to reduce a voltage drop caused by the RC distributed constant circuit of the thin film piezoelectric element array, and obtain a greater sound pressure compared to a one-sided voltage application method.

Figure 11A:
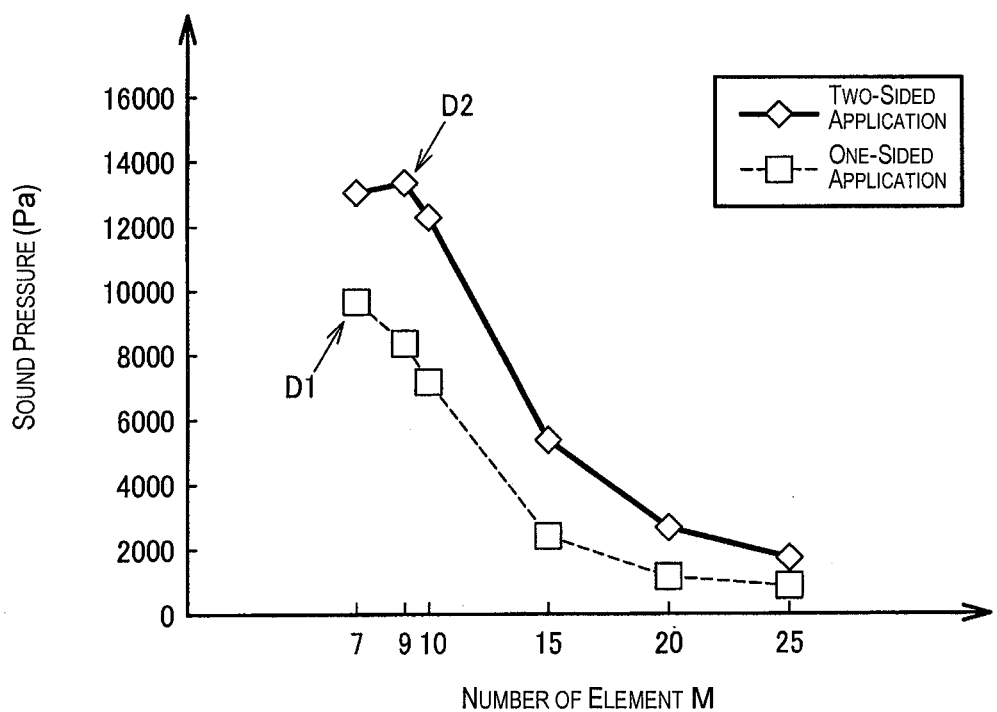
FIG. 11A and FIG. 11B show examples of characteristics of the sound pressure in the center when the number "M" of columns of elements is changed.
Figure 11B:
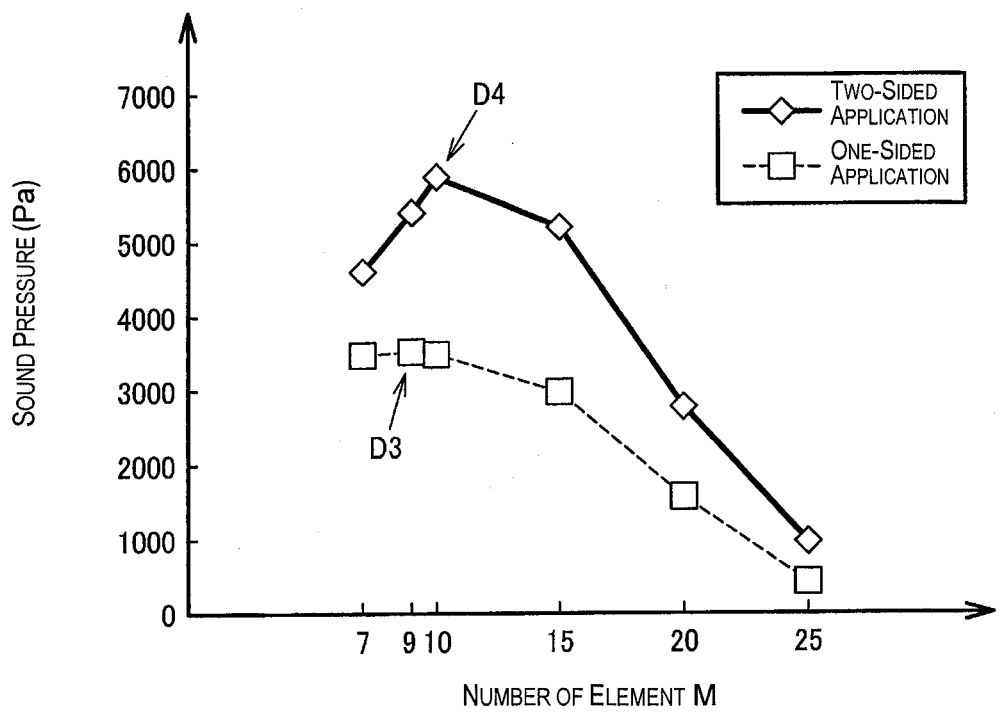

Next, the sound pressure in the center x=0 of the element column (the sound pressure in the center) will be explained in more detail. FIG. 11A and FIG. 11B show examples of characteristics of the sound pressure in the center when the number "M" of elements in a column is changed. The simulation conditions are the same as those of the comparative example of FIG. 3A to FIG. 5B and the present embodiment of FIG. 8A to FIG. 10B.

FIG. 11A shows simulation results at a depth of 10 mm when the frequency of a driving voltage is 3.5 MHz. D1 and D2 show simulation results of a one-sided voltage application method and a two-sided voltage application method, respectively. As shown in D1 and D2, a higher sound pressure in the center can be obtained and stronger ultrasonic beams can be emitted in the two-sided voltage application method irrespective of the number "M". Although the sound pressure in the center decreases due to a voltage drop as the number "M" increases in either method, the sound pressure in the center reaches the maximum in the one-sided voltage application method when the number "M" is 7, while the sound pressure in the center reaches the maximum in the two-sided voltage application method when the number "M" is 9. This is because the voltage drop is reduced by using the two-sided voltage application method, and this shows that a higher sound pressure in the center can be achieved by increasing the number "M" of the elements in the two-sided voltage application method compared to the one-sided voltage application method.

FIG. 11B shows simulation results at a depth of 30 mm when the frequency of a driving voltage is 3.5 MHz. D3 and D4 show simulation results of a one-sided voltage application method and a two-sided voltage application method, respectively. As shown in D3 and D4, the sound pressure in the center reaches the maximum in the one-sided voltage application method when the number "M" is 9, and the sound pressure in the center reaches the maximum in the two-sided voltage application method when the number "M" is 10. In the same manner as FIG. 11A, this shows that a higher sound pressure in the center can be achieved by increasing the number "M" of the elements in the two-sided voltage application method compared to the one-sided voltage application method.

4. Driving Voltage Output Circuit

Figure 12:
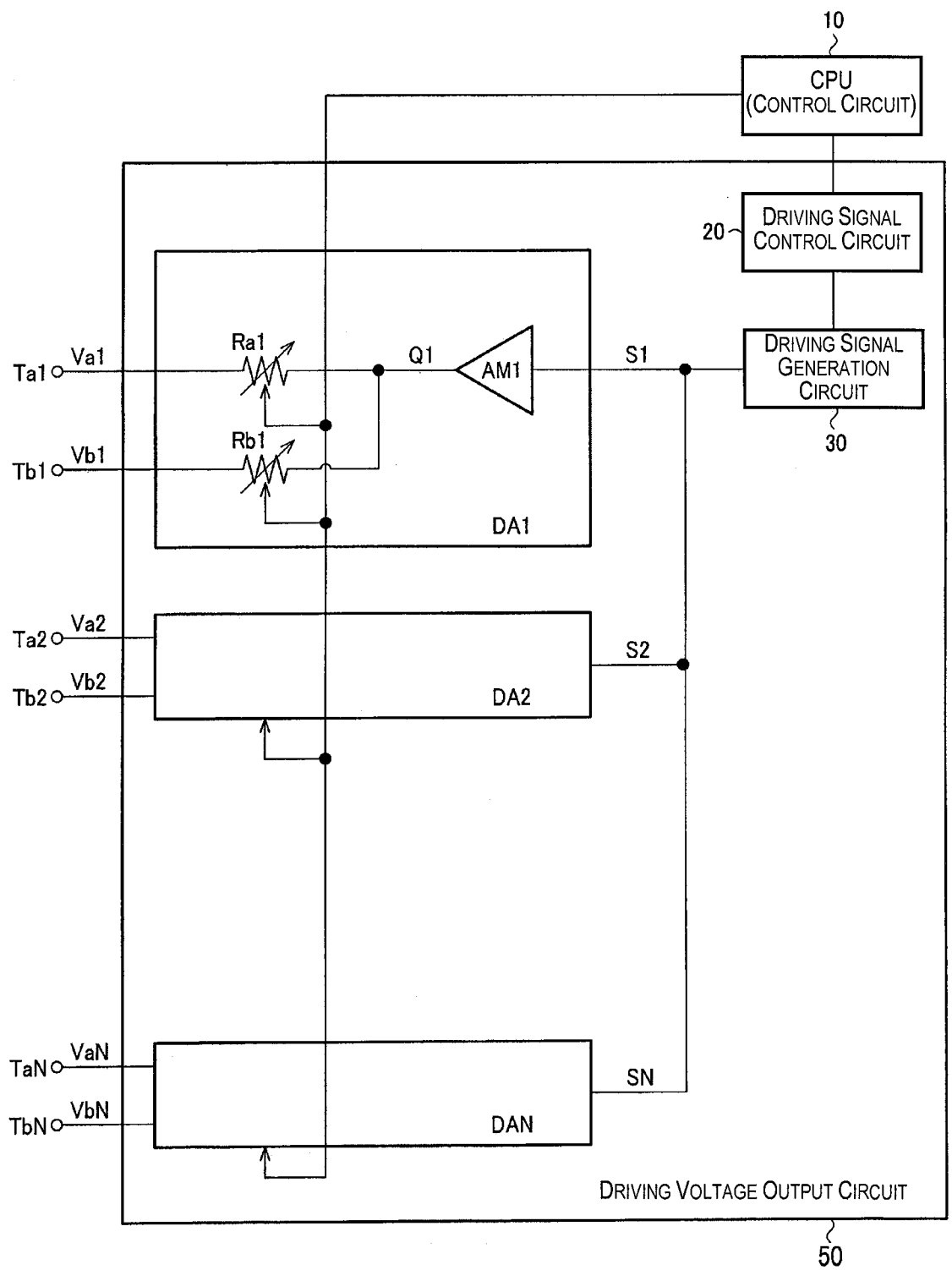
FIG. 12 shows the details of a configuration example of a driving voltage output circuit.

FIG. 12 shows the details of a configuration example of a driving voltage output circuit that outputs the above-described driving voltage. The driving voltage output circuit 50 shown in FIG. 12 includes a driving signal control circuit 20, a driving signal generation circuit 30, and a driving amplifier circuits DA1-DAN. The driving voltage output circuit may be included in the ultrasonic device (the element chip 200 of FIG. 18) or may be included in the processing device (the processing device 330 of FIG. 18).

The driving signal control circuit 20 controls the driving signal generation circuit 30 based on control instructions from a CPU 10 (control circuit). For example, the driving signal control circuit 20 controls phase scanning by controlling the phase of driving signals S1-SN, and controls the sound pressure of ultrasonic waves by controlling the amplitude of the driving signals S1-SN. The driving signal generation circuit 30 outputs the driving signals S1-SN to the driving amplifier circuits DA1-DAN based on the control from the driving signal control circuit 20.

The driving amplifier circuits DA1-DAN amplify the driving signals S1-SN, and output driving voltages Va1-VaN, Vb1-VbN to the driving terminals Ta1-TaN, Tb1-TbN. Hereinafter, a detailed configuration example of the driving amplifier circuit DA1 will be explained as an example. The driving amplifier circuits DA2-DAN are the same.

The driving amplifier circuit DA1 includes an amplifier circuit AM1, and variable resistances Ra1, Rb1. The amplifier circuit AM1 amplifies the signal S1 and outputs a voltage Q1 (or current). In the variable resistances Ra1, Rb1, the resistances are controlled to be variable based on the control from the CPU 10. When the resistance value of the variable resistance Ra1 is set to be smaller than the resistance value of the variable resistance Rb1, the amplitude of the voltage of the terminal Ta1 becomes greater than the amplitude of the voltage of the terminal Tb1. On the other hand, when the resistance value of the variable resistance Ra1 is set to be greater than the resistance value of the variable resistance Rb1, the amplitude of the voltage of the terminal Ta1 becomes smaller than the amplitude of the voltage of the terminal Tb1. When the resistance value of the variable resistance Ra1 and the resistance value of the variable resistance Rb1 are set to be the same value, the amplitude of the voltage of the terminal Ta1 and the amplitude of the voltage of the terminal Tb1 become the same.

Figure 13A:
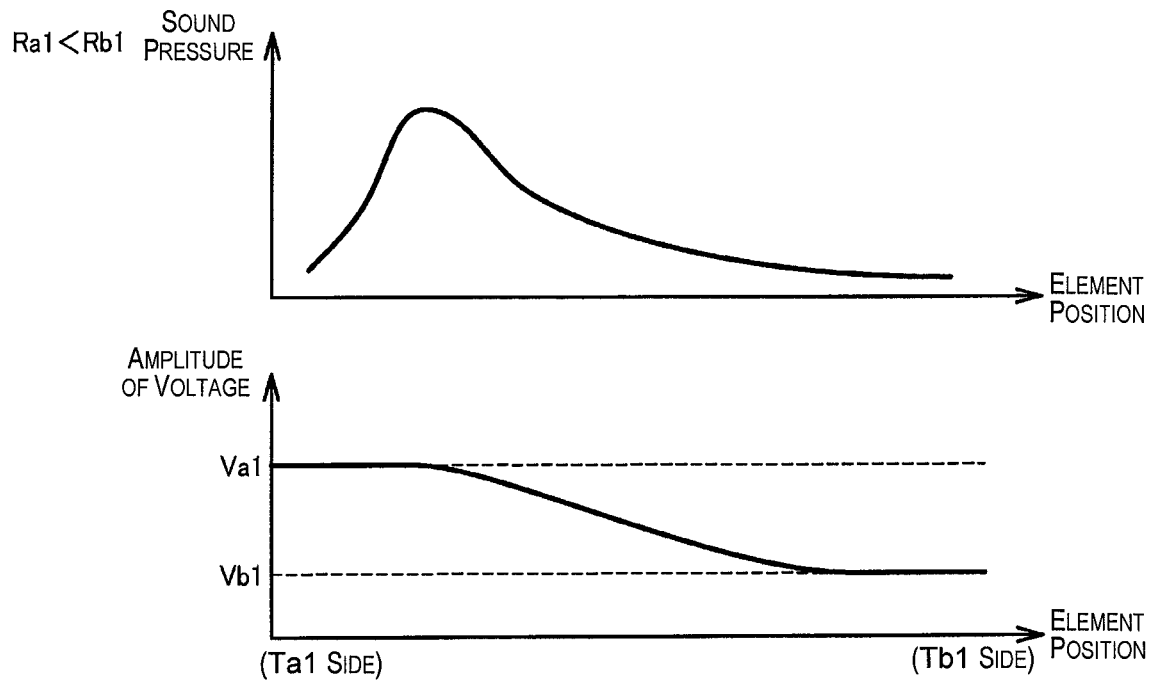
FIG. 13A and FIG. 13B show examples of characteristics of the amplitude of a voltage in a column of ultrasonic elements and examples of characteristics of the sound pressure distribution when the driving voltage output circuit is used.
Figure 13B:
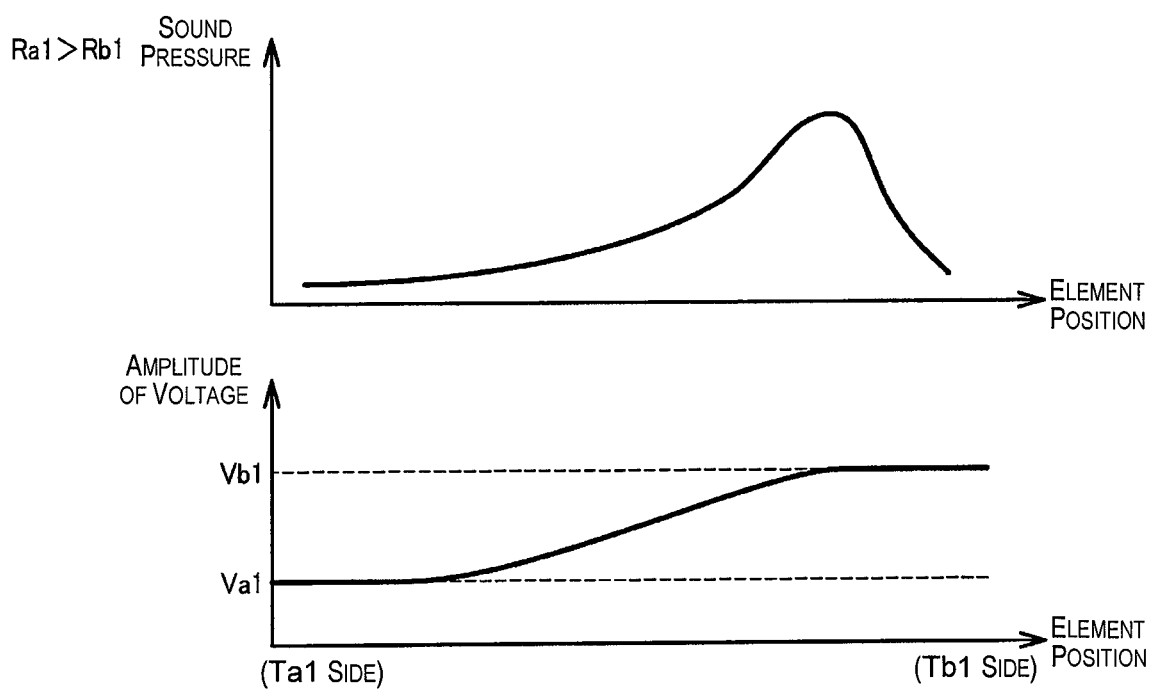

FIG. 13A and FIG. 13B schematically show examples of characteristics of the amplitude of a voltage in columns of elements Pl1-PM1, and examples of characteristics of the sound pressure distribution when the driving voltage output circuit 50 is used.

As shown in FIG. 13A, when the variable resistances are set to be Ra1<Rb1, the amplitude of the voltage becomes Va1>Vb1, and the amplitude decreases from the terminal Ta1 side to the terminal Tb1 side. Therefore, the radiated sound pressure distribution of ultrasonic waves is shifted from the center of the element column to the terminal Ta1 side. As shown in FIG. 13B, when the variable resistances are set to be Ra1>Rb1, the amplitude of the voltage becomes Va1<Vb1, and the amplitude decreases from the terminal Tb1 side to the terminal Ta1 side. Therefore, the radiated sound pressure distribution of ultrasonic waves is shifted from the center of the element column to the terminal Tb1 side. In this manner, by adjusting the resistance values of the variable resistances, the sound pressure distribution can be shifted to the slice direction while achieving advantages of the two-sided voltage application method.

Further, when the resistance values of the variable resistances Ra1, Rb1 are made large, the amplitudes of the voltages Va1, Vb1 become small, and the peak value of the radiated sound pressure becomes small. When the resistance values of the variable resistances Ra1, Rb1 are made small, the amplitudes of the voltages Va1, Vb1 become large, and the peak value of the radiated sound pressure becomes large. Consequently, the peak value of the radiated sound pressure can be adjusted by adjusting the resistance values of the variable resistances Ra1, Rb1 as well as by adjusting the driving signals S1-SN.

According to the above-described present embodiment, as shown in FIG. 6, the ultrasonic device includes the group of ultrasonic elements Pl1-PMN in which "N" columns of ultrasonic elements are arranged along the second direction D2 that intersects with the first direction D1, each column including the plurality of ultrasonic elements Pli-PMi arranged along the first direction D1, the first to the $N^{th}$ driving electrode lines SL1-SLN arranged along the first direction D1 ("N" is a natural number that is equal to or more than 2), the first terminal Tai, and the second terminal Tbi. The $i^{th}$ driving electrode line SLi among the first to the $N^{th}$ driving electrode lines SLi-SLN ("i" is a natural number that is equal to or less than "N") is connected to the ultrasonic elements Pli-PMi constituting the $i^{th}$ column of ultrasonic elements among the "N" columns of ultrasonic elements. The first terminal Tai is connected to one end of the $i^{th}$ driving electrode line SLi, and the second terminal Tbi is connected to the other end of the $i^{th}$ driving electrode line SLi.

As explained in FIG. 6, the ultrasonic element is not limited to a thin film piezoelectric element, and it is sufficient for the ultrasonic element to be an element that converts electric signals (driving voltage or driving current) into ultrasonic waves. Further, the driving signals supplied to the terminals Tai, Tbi are not limited to the driving voltages Va1, Vb1, and may be driving current. Furthermore, the number of the columns of ultrasonic elements constituting the group of ultrasonic elements is not limited to "N" columns described above ("N" is a natural number that is equal to or more than 2), and one column may be possible.

The group of ultrasonic elements in which "N" columns of ultrasonic elements are arranged is not limited to the arrangement of the matrix pattern. It is sufficient for the arrangement to be an array pattern in which a plurality of unit elements are arranged two-dimensionally with regularity. For example, the group of ultrasonic elements may be arranged in a zigzag pattern. The arrangement of the matrix pattern is a grid-pattern arrangement of "M" rows and "N" columns, which includes a case where the grid is deformed to be a parallelogram as well as a case where the grid is a rectangle. The arrangement of the zigzag pattern is an arrangement in which a column of "M" ultrasonic elements and a column of "M−1" ultrasonic elements are alternately arranged, and the ultrasonic elements of the column of the "M" ultrasonic elements are arranged in an odd number row among (2M−1) rows and the ultrasonic elements of the column of the "M−1" ultrasonic elements are arranged in an even number row among (2M−1) rows.

As explained with reference to FIG. 1 to FIG. 5B, since the RC distributed constant circuit is formed by the parasitic capacitance of the ultrasonic element and the parasitic resistance of the wiring, the amplitude of the driving signal applied to the electrodes of an ultrasonic element is decreased in an ultrasonic element that is farther away from the end to which the driving signal is input. Therefore, the one-sided voltage application method has a problem that the radiated sound pressure distribution of ultrasonic waves has asymmetric characteristics or the sound pressure is decreased.

In this regard, according to the present embodiment, the terminals Tai, Tbi for supplying a driving signal to the group of ultrasonic elements Pl1-PMN are provided on both ends of the driving electrode line SLi. As explained with reference to FIG. 7 and the like, this configuration makes it possible to apply a driving signal from both ends of the column of ultrasonic elements connected to the driving electrode line SLi, which results in characteristics in which the amplitude of the driving signal is decreased from both ends of the element column toward the center. Therefore, the sound pressure distribution is allowed to converge to the center of the element column. Also, since the amplitude of the driving signal can be prevented from being decreased, the radiated sound pressure can be improved compared to the one-sided voltage application method without increasing the number of the ultrasonic elements. Further, since a smaller number of ultrasonic elements is sufficient to achieve a similar radiated sound pressure compared to the one-sided voltage application method, the size of the ultrasonic element array 100 can be reduced.

According to the present embodiment, the number "M" of the ultrasonic elements Pli-PMi arranged in the column of ultrasonic elements is equal to or less than "m" ("m" is a natural number that is equal to or more than 3).

As explained with reference to FIG. 11A, FIG. 11B, and the like, the sound pressure in the center of the element column at a predetermined depth reaches the maximum when the number "M" is changed. However, it is not that the sound pressure in the center of the element column increases when the number "M" is increased. In this regard, according to the present embodiment, by setting the upper limit of the number "M", the area of the ultrasonic element array 100 can be saved while obtaining a large sound pressure. More specifically, "m" can be set such that the number "M" which makes the sound pressure maximum is within the range of being equal to or more than 3 and equal to or less than "m". For example, the number "M" which makes the peak sound pressure half of the maximum when the number "M" is changed can be set as "m".

According to the present embodiment, the number "M" may be set to be equal to or less than m=a in a case where "a" ("a" is a natural number that is equal to or more than 3) is the number of ultrasonic elements arranged in the first direction D1 when the sound pressure of the center of the column of ultrasonic elements is half of the peak with respect to the sound pressure distribution characteristics in the first direction D1 of ultrasonic waves output from the ultrasonic element array 100 in a case where a driving signal is input only to the first terminal Tai.

Here, the center of the column of ultrasonic elements refers to a position that divides the number of the ultrasonic elements Pli-PMi constituting the column of ultrasonic elements into halves. Specifically, when the number "M" is an even number 2k ("k" is a natural number), the center of the column of ultrasonic elements is an intermediate position between the $k^{th}$ ultrasonic element from one end of the column of ultrasonic elements and the $k^{th+1}$ ultrasonic element. When the number "M" is an odd number 2k+1, the center of the column of ultrasonic elements is a position of the $k^{th+1}$ ultrasonic element from one end of the column of ultrasonic elements.

The "peak of sound pressure" in a case of inputting a driving signal only to the first terminal Tai refers to a peak in which the sound pressure is maximum with respect to the sound pressure characteristics of ultrasonic waves. For example, the sound pressure characteristics at a depth of 10 mm shown in FIG. 4B have a plurality of small peaks other than a peak of the sound pressure of 6980 Pa. However, the peak of the sound pressure of 6980 Pa is called as the "peak of sound pressure". The "peak of sound pressure" in a case of inputting a driving signal to both of the first and second terminals Tai, Tbi is, for example, 8757 Pa in FIG. 9B, and a peak (8352 Pa) in a symmetric position of the peak of the maximum sound pressure with respect to x=0. When the peak (12277 Pa) of the maximum sound pressure is located in x=0 as shown in FIG. 8B, the peak is the "peak of sound pressure".

For example, in the present embodiment, the one-sided voltage application method and the two-sided voltage application method will be compared by taking the sound pressure distribution characteristics at a depth of 30 mm as an example. In the one-sided voltage application method, as shown in FIG. 3B, the peak is 7160 Pa in the center of the element column x=0 when the number "M" is 10. As shown in FIG. 4B and FIG. 5B, the sound pressure in the center of the element column x=0 is smaller than half of the peak 6980 Pa and 6875 Pa when the number "M" is 15 and 20, respectively. In other words, the number "M" that makes the sound pressure in the center of the element column x=0 half of the peak is more than 10 and less than 15. In this case, in the two-sided voltage application method, as shown in FIG. 8B, the peak is 12277 Pa in the center of the element column x=0 when the number "M" is 10, and as shown in FIG. 9B and FIG. 10B, the center of the element column x=0 is not a peak when the number "M" is 15 and 20. This shows that ultrasonic beams do not converge to the center.

In this regard, according to the present embodiment, the number "M" that makes the sound pressure in the center of the element column half of the peak in the one-sided voltage application method is M=a, the number "M" can be set to be equal to or less than "a". With this, ultrasonic beams are allowed to converge to the center (or one). For example, in the example of the depth of 30 mm, "a" is a number that is more than 10 and less than 15 in the one-sided voltage application method. When the number "M" is less than "a" in the two-sided voltage application method, it is possible to eliminate the number "M" of 15 and 20 in which ultrasonic waves do not converge.

According to the present embodiment, m=b may be possible in a case where the sound pressure distribution characteristics in the first direction D1 of ultrasonic waves output from the group of ultrasonic elements Pl1-PMN have double peaks when the number of ultrasonic elements arranged in the first direction D1 is b+1 ("b" is a natural number that is equal to or more than 3), and have a single peak when the number of ultrasonic elements arranged in the first direction D1 is "b" in a case where a driving signal is input to the first terminal Tai and the second terminal Tbi.

Here, the single peak indicates that there is one peak in the sound pressure distribution characteristics at a predetermined depth. Specifically, as shown in the sound pressure distribution characteristics at a depth of 30 mm of FIG. 8B, for example, it has symmetric characteristics with respect to the symmetry axis (for example, the center of the element column x=0). The maximum value of the sound pressure is located on the symmetry axis.

The double peaks indicate that there are two peaks in the sound pressure distribution characteristics at a predetermined depth. Specifically, as shown in the sound pressure distribution characteristics at a depth of 30 mm of FIG. 9B, for example, it has symmetric characteristics with respect to the symmetry axis (for example, the center of the element column x=0). The maximum value of the sound pressure is not located on the symmetry axis. The first peak of 8757 Pa in which the sound pressure is maximum and the second peak of 8352 Pa which is similar to the sound pressure of the first peak (for example, 90% or more of the sound pressure of the first peak) is located in a position of x=+1.5 mm which is symmetric with respect to the symmetry axis.

With this, a maximum number M=b that can maintain a single peak when the number "M" is increased can be set to be a maximum value "m" of the number "M". Consequently, a single peak can be achieved in the sound pressure distribution characteristics at a predetermined depth, and ultrasonic beams are allowed to converge to one.

According to the present embodiment, as shown in FIG. 12, the ultrasonic device includes a driving signal output circuit (driving voltage output circuit 50) that outputs a driving signal (driving voltage Vai, Vbi) for driving the group of ultrasonic elements Pl1-PMN to the first terminal Tai and the second terminal Tbi.

More specifically, the driving signal output circuit outputs a driving signal (driving voltage Vai, Vbi) having different amplitude to the first terminal Tai and the second terminal Tbi.

With this, as explained with reference to FIG. 13A and FIG. 13B, by adjusting the amplitude of the driving signal output to the terminals Tai, Tbi, the peak position of ultrasonic beams can be adjusted in the slice direction (D1 of FIG. 6).

According to the present embodiment, as shown in FIG. 12, the driving signal output circuit has an output amplifier AMi ("i"=1, for example, in the driving amplifier circuit DA1), a first variable resistance Rai for adjusting the amplitude of the driving signal to the first terminal Tai provided between the output amplifier AMi and the first terminal Tai, and a second variable resistance Rbi for adjusting the amplitude of the driving signal to the second terminal Tbi provided between the output amplifier AMi and the second terminal Tbi.

With this, by adjusting the resistance values of the variable resistances Rai, Rbi, the amplitude of the driving signal (driving voltage Vai, Vbi) output to the terminals Tai, Tbi can be adjusted.

According to the present embodiment, as shown in FIG. 6, the ultrasonic device includes the plurality of common electrode lines CL1-CLM that are arranged along the second direction D2.

More specifically, the $j^{th}$ common electrode line CLj among the first to the $M^{th}$ common electrode lines CL1-CLM as the plurality of common electrode lines is connected to the $j^{th}$ ultrasonic element Pji among the first to the $M^{th}$ ultrasonic elements Pli-PMi that constitute the $i^{th}$ column of the ultrasonic element.

With this, by arranging the plurality of common electrode lines CL1-CLM instead of one solid common electrode line, the driving electrode lines and the common electrode lines can be insulated by the ultrasonic elements (thin film piezoelectric elements). Consequently, there is no need to provide an insulating layer for insulating the driving electrode lines and the common electrode lines other than the ultrasonic elements.

According to the present embodiment, as shown in FIG. 6, the ultrasonic device includes the shared common electrode lines AL1, AL2 that are connected to the plurality of common electrode lines CL1-CLM in common and arranged along the first direction D1.

According to the present embodiment, the ultrasonic device includes the terminals CTa1, CTb1, CTa2, and CTb2 for supplying a common voltage to the group of ultrasonic elements Pl1-PMN that are provided at both ends of the shared common electrode lines AL1, AL2.

With this, the plurality of common electrode lines CL1-CLM can be combined into the shared common electrode lines AL1, AL2. Also, a common voltage can be supplied from the terminals CTa1, CTb1, CTa2, and CTb2 in common with respect to the plurality of common electrode lines CL1-CLM.

5. Ultrasonic Transducer Element

Figure 14A:
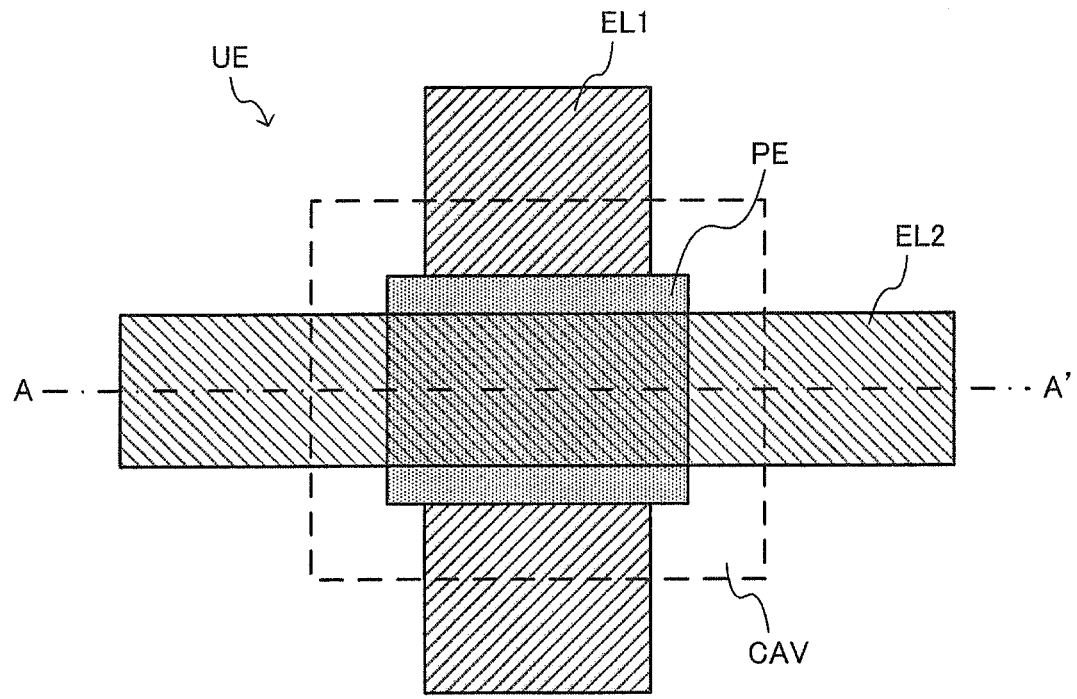
FIG. 14A and FIG. 14B show a configuration example of the ultrasonic element.
Figure 14B:
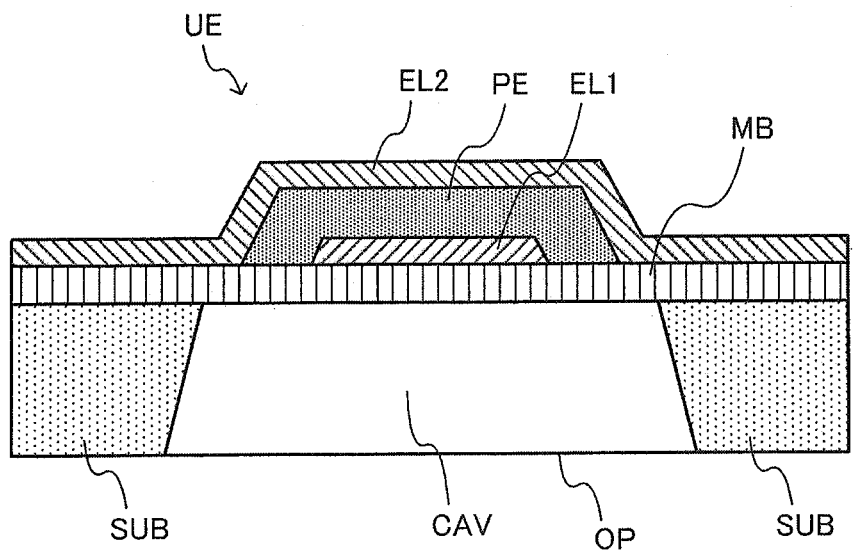

FIG. 14A and FIG. 14B show a configuration example of an ultrasonic element that constitutes the group of ultrasonic elements Pl1-PMN. Hereinafter, when appropriate, the ultrasonic element is also called as the ultrasonic transducer element.

The ultrasonic transducer element UE shown in FIG. 14A and FIG. 14B includes a first electrode layer EL1, a piezoelectric body layer PE, a second electrode layer EL2, a membrane (supporting member) MB, and a cavity region (cavity section) CAV. The ultrasonic transducer element UE according to the present embodiment is not limited to the configuration of FIG. 14, and various changes and modifications are possible. For example, a part of its components can be omitted or replaced with other components, or other components can be added.

FIG. 14A is a plan view of the ultrasonic transducer element UE formed on a substrate (silicon substrate) SUB, seen from a direction perpendicular to the substrate on a side where the element is formed. FIG. 14B is a sectional view along line A-A' of FIG. 14A.

The first electrode layer EU is formed on an upper layer of the membrane MB as a metal thin film, for example. The first electrode layer (lower electrode layer) EU may be a wiring extended outside a region in which the element is formed as shown in FIG. 14A, and connected to the adjacent ultrasonic transducer element UE.

The piezoelectric body layer PE is formed of a PZT (piezoelectric zirconate titanate) thin film, for example. The piezoelectric body layer PE is arranged to cover at least a part of the first electrode layer EU. The material of the piezoelectric body layer PE is not limited to PZT. Lead titanate ($PbTiO_3$), lead zirconate ($PbZrO_3$), lead lanthanum titanate (($Pb, La)TiO_3$), or the like may be used.

The second electrode layer (upper electrode layer) EL2 is formed of a metal thin film, for example, and is arranged to cover at least a part of the piezoelectric body layer PE. The second electrode layer EL2 may be a wiring extended outside the region in which the element is formed as shown in FIG. 14A, and connected to the adjacent ultrasonic transducer element UE.

The membrane MB is provided on an upper layer of the cavity region CAV with a two-layer configuration made of an $SiO_2$ thin film and a $ZrO_2$ thin film, for example. The membrane MB supports the piezoelectric body layer PE, the first electrode layer EU and the second electrode layer EL2. The membrane MB vibrates in accordance with expansion and contraction of the piezoelectric body layer PE so as to generate ultrasonic waves.

The cavity region CAV is formed from a reverse surface (in which no element is formed) of the silicon substrate SUB by etching such as reactive ion etching (RIE). Ultrasonic waves are emitted from an opening OP of the cavity region CAV.

A first electrode of the ultrasonic transducer element UE is formed of the first electrode layer EL1 and a second electrode of the ultrasonic transducer element UE is formed of the second electrode layer EL2. More specifically, a part of the first electrode layer EL1 that is covered by the piezoelectric body layer PE forms the first electrode, and a part of the second electrode layer EL2 that covers the piezoelectric body layer PE forms the second electrode. In other words, the piezoelectric body layer PE is sandwiched by the first electrode and the second electrode.

The piezoelectric body layer PE expands or contracts in an in-plane direction when a voltage is applied between the first electrode and the second electrode, that is, between the first electrode layer EL1 and the second electrode layer EL2. One surface of the piezoelectric body layer PE is attached to the membrane MB through the first electrode layer EL1. Although the second electrode layer EL2 is formed on the other surface of the piezoelectric body layer PE, no other layer is formed on the second electrode layer EL2. Therefore, the piezoelectric body layer PE is difficult to expand or contract on the membrane MB side, and the piezoelectric body layer PE is easy to expand or contract on the second electrode layer EL2 side. Accordingly, when a voltage is applied to the piezoelectric body layer PE, convex warpage occurs on the cavity region CAV side, which causes the membrane MB to warp. When an alternating-current voltage is applied to the piezoelectric body layer PE, the membrane MB vibrates in a film thickness direction, and ultrasonic waves are emitted from the opening OP by the vibration of the membrane MB. The voltage applied to the piezoelectric body layer PE is 10-30 V, for example. The frequency is 1-10 MHz, for example.

6. Head Unit

Figure 15:
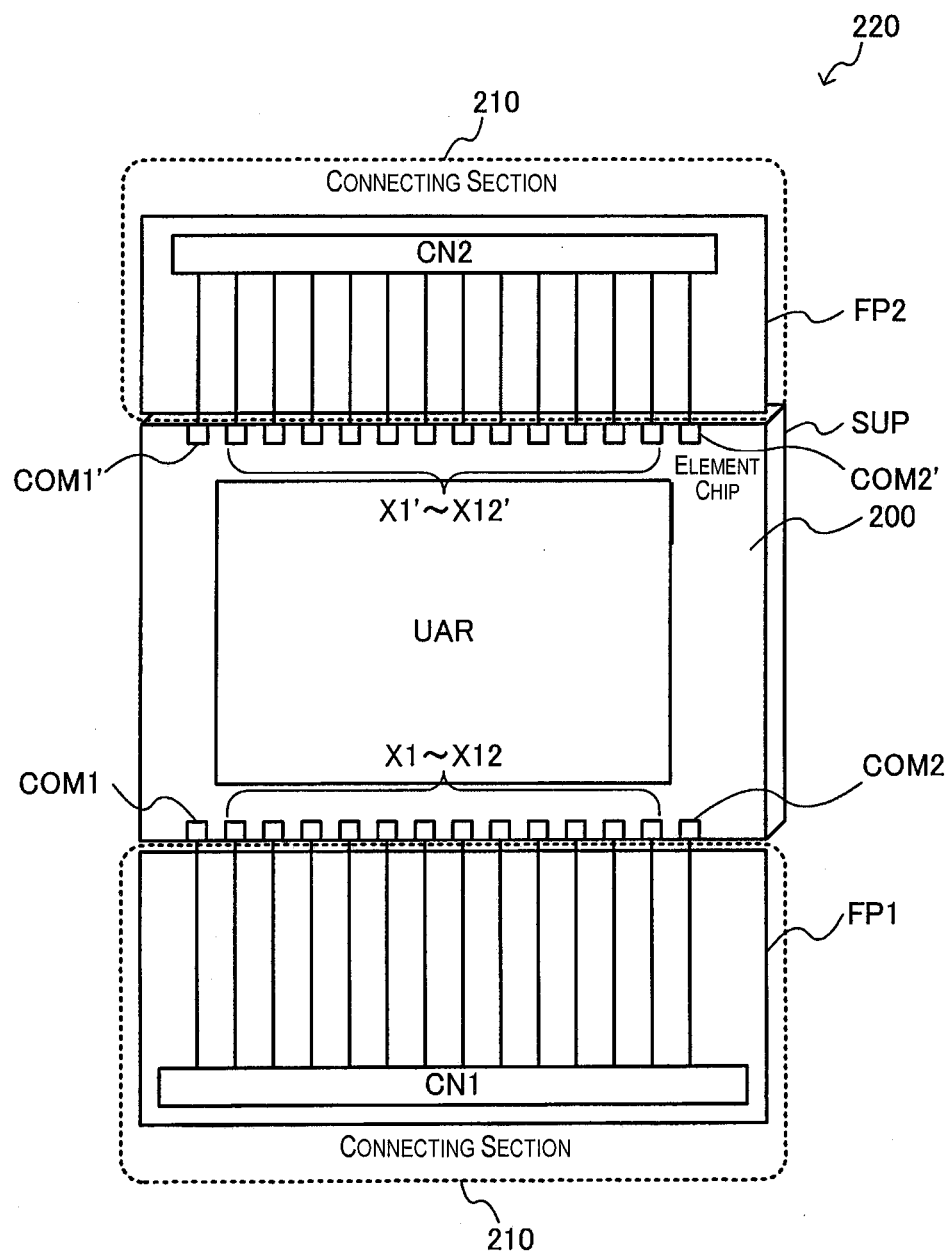
FIG. 15 shows a configuration example of a head unit.

FIG. 15 shows a configuration example of a head unit 220 in which the ultrasonic device of FIG. 6 is installed. The head unit 220 shown in FIG. 15 includes the element chip 200, a connecting section 210, and a supporting member SUP. The head unit 220 according to the present embodiment is not limited to the configuration of FIG. 15, and various changes and modifications are possible. For example, a part of its components can be omitted or replaced with other components, or other components can be added.

The element chip 200 corresponds to the ultrasonic device explained with reference to FIG. 6. The element chip 200 includes an ultrasonic element array UAR, signal terminals (first group of chip terminals in a broad sense) X1-X12, signal terminals (second group of chip terminals in a broad sense) X1'-X12', and common terminals COM1, COM2, COM1', and COM2'. The signal terminals X1-X12 correspond to the terminals Ta1-Ta12 (for example, N=12) of FIG. 6. The signal terminals X1'-X12' correspond to the terminals Tb1-Tb12 of FIG. 6. The common terminals COM1, COM2, COM1', and COM2' correspond to the terminals CTa1, CTb1, CTa2, and CTb2 of FIG. 6. The element chip 200 is electrically connected to a processing device (the processing device 330 of FIG. 18, for example) of a probe main body through the connecting section 210.

The connecting section 210 electrically connects the probe main body and the head unit 220. The connecting section 210 has a connector CN that has a plurality of connecting terminals, and a flexible substrate FP on which a wiring connecting the connector CN and the element chip 200 is formed. Specifically, the connecting section 210 has a first connector CN1 and a second connector CN2 as the connector, and also has a first flexible substrate FP1 and a second flexible substrate FP2 as the flexible substrate.

In the first flexible substrate FP1, there is provided a first group of wirings that connects the first group of chip terminals X1-X12 arranged on the side of a first side of the element chip 200 to the first connector CN1. Also, in the second flexible substrate FP2, there is provided a second group of wirings that connects the second group of chip terminals X1'-X12' arranged on the side of a second side of the element chip 200 opposite to the first side to the second connector CN2.

The connector CN1 has the plurality of connecting terminals where a signal of the first group of chip terminals X1-X12 is input or output through the first group of wirings formed on the flexible substrate FP1. The connector CN2 has the plurality of connecting terminals where a signal of the second group of chip terminals X1'-X12' is input or output through the second group of wirings formed on the flexible substrate FP2.

The connecting section 210 is not limited to the configuration of FIG. 15. The connecting section 210 may have a first group of connecting terminals where a signal of the first group of chip terminals arranged on the side of the first side of the element chip 200 is input or output, and a second group of connecting terminals where a signal of the second group of chip terminals arranged on the side of the second side of the element chip 200 opposite to the first side is input or output.

With the connecting section 210, the probe main body and the head unit 220 can be electrically connected, and the head unit 220 can be removable with respect to the probe main body.

The supporting member SUP is a member for supporting the element chip 200. As described below, the plurality of connecting terminals are arranged on a first surface side of the supporting member SUP. The element chip 200 is supported on a second surface side of the supporting member SUP. The second surface is a reverse surface of the first surface. The detailed configurations of the element chip 200, the connecting section 210, and the supporting member SUP will be described below.

FIG. 16A-FIG. 16C show the details of the configuration example of the head unit 220. FIG. 16A shows the second surface SF2 side of the supporting member SUP, FIG. 16B shows the first surface SF1 side of the supporting member SUP, and FIG. 16C shows a side surface side of the supporting member SUP. The head unit 220 according to the present embodiment is not limited to the configuration of FIG. 16A-FIG. 16C, and various changes and modifications are possible. For example, a part of its components can be omitted or replaced with other components, or other components can be added.

The connectors CN1, CN2 (connecting terminals in a broad sense) are arranged on the first surface SF1 side of the supporting member SUP. One ends of the flexible substrates FP1, FP2 are connected to the connectors CN1, CN2, respectively. Circuits such as preamplifiers PA1, PA2 may be provided on the flexible substrates FP1, FP2. The connectors CN1, CN2 are configured to be removable with respect to the corresponding connectors of the probe main body.

The element chip 200 is supported on the second surface SF2 side of the supporting member SUP. The second surface SF2 is a reverse surface of the first surface SF1. The other ends of the flexible substrates FP1, FP2 are connected to the terminals of the element chip 200. A fixing member HL is provided in each corner portion of the supporting member SUP, and is used for fixing the head unit 220 to a probe case.

The first surface side of the supporting member SUP refers to a normal direction side of the first surface SF1 of the supporting member SUP, and the second surface side of the supporting member SUP refers to a normal direction side of the second surface SF2 that is a reverse surface of the first surface SF1 of the supporting member SUP.

As shown in FIG. 16C, a protective member (protective film) PF for protecting the element chip 200 is provided in a reverse surface of the element chip 200 (surface in which the opening OP is provided in FIG. 14B).

7. Ultrasonic Probe

Figure 17A:
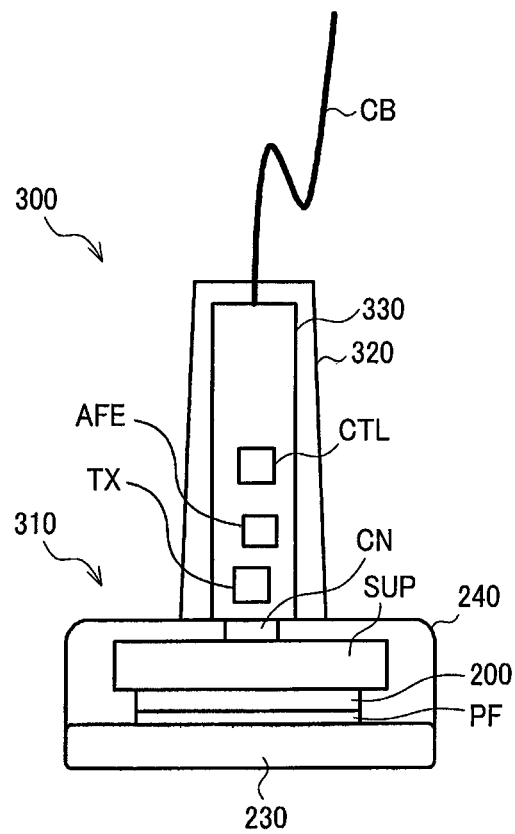
FIG. 17A and FIG. 17B show a configuration example of an ultrasonic probe.
Figure 17B:
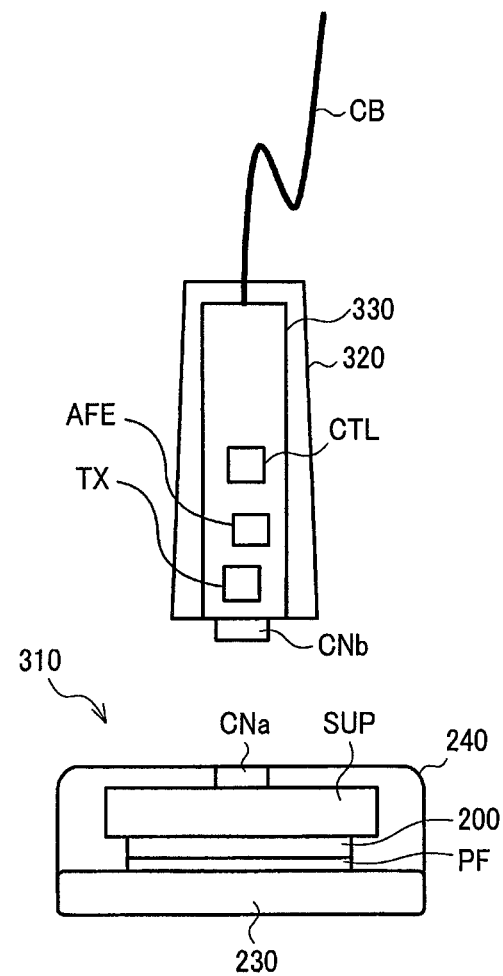

FIG. 17A and FIG. 17B show a configuration example of an ultrasonic probe 300 to which the above-described head unit 220 is applied. FIG. 17A shows a case where a probe head 310 is mounted to a probe main body 320, and FIG. 17B shows a case where the probe head 310 is separated from the probe main body 320.

The probe head 310 includes the head unit 220, a contact member 230 that contacts a material to be tested, and a probe case 240 for storing the head unit 220. The element chip 200 is provided between the contact member 230 and the supporting member SUP.

The probe main body 320 has the processing device 330 and a probe main body side connector CNb. The processing device 330 has a transmitting section TX, an analog front-end section AFE, and a controlling section CTL. Based on control of the controlling section CTL, the transmitting section TX conducts processing of transmitting a driving signal for driving the ultrasonic transducer element, and the analog front-end section AFE conducts processing of receiving an ultrasonic echo signal (received signal) from the ultrasonic transducer element.

The controlling section CTL controls the transmitting section TX and the analog front-end section AFE. The probe main body side connector CNb is connected to a head unit (or probe head) side connector CNa. The probe main body 320 is connected to a main electronic instrument (for example, ultrasonic diagnostic device) through a cable CB.

Although the head unit 220 is stored in the probe case 240, the head unit 220 can be removed from the probe case 240. With this, only the head unit 220 can be replaced. It is also possible to replace in a state of being stored in the probe case 240, that is, as the probe head 310.

8. Ultrasonic Diagnostic Device

Figure 18:
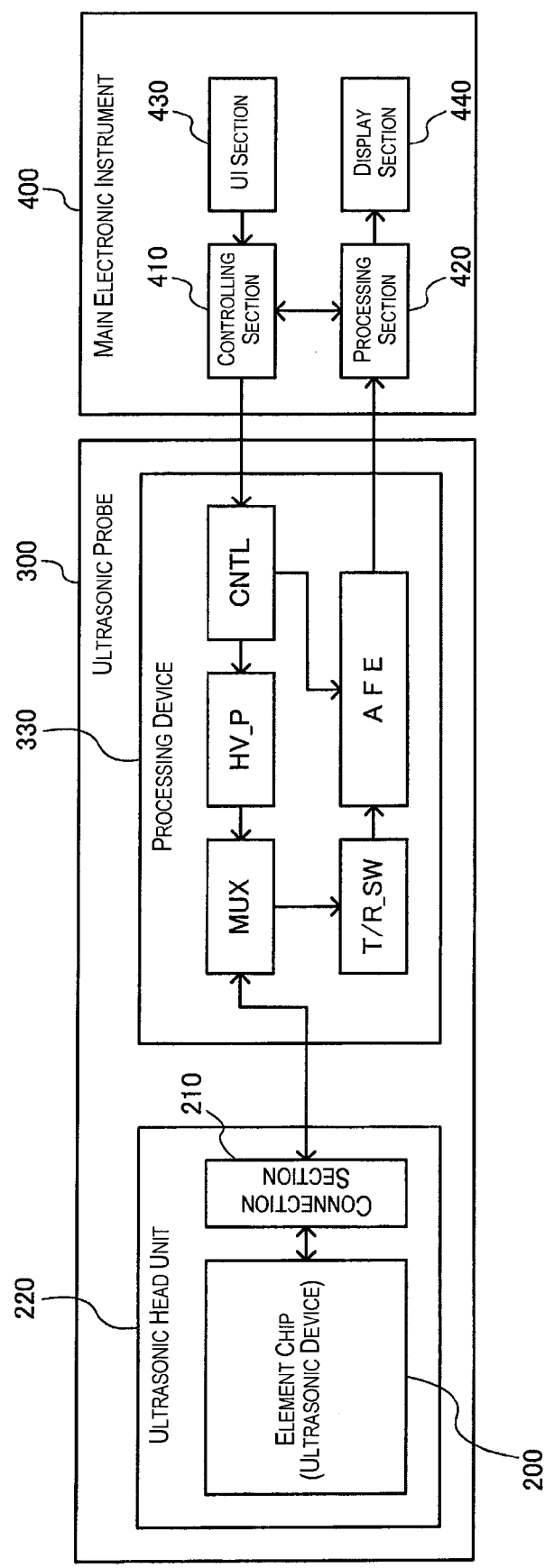
FIG. 18 shows a configuration example of an ultrasonic diagnostic device.

FIG. 18 shows a configuration example of an ultrasonic diagnostic device. The ultrasonic diagnostic device includes the ultrasonic probe 300 and a main electronic instrument 400. The ultrasonic probe 300 includes the ultrasonic head unit 220 and the processing device 330. The main electronic instrument 400 includes a controlling section 410, a processing section 420, a user interface section 430, and a display section 440.

The processing device 330 includes a selecting section MUX, a switching section T/R_SW, a transmitting section HV_P, a transmission and reception controlling section CNTL, and a receiving section AFE (analog front-end section). The ultrasonic head unit 220 includes the element chip 200 (ultrasonic device), and the connecting section 210 (connector section) that connects the element chip 200 to a circuit substrate. The selecting section MUX, the transmitting section HV_P, the transmission and reception controlling section CNTL, the switching section T/R_SW, and the receiving section AFE are mounted to the circuit substrate.

When ultrasonic waves are transmitted, the transmission and reception controlling section CNTL issues transmission instructions to the transmitting section HV_P. The transmitting section HV_P receives the transmission instructions, amplifies a driving signal to a high voltage, and outputs a driving voltage. The selecting section MUX outputs the driving signal to the element chip 200. In this instance, the switching section T/R_SW is turned off. When reflected waves of ultrasonic waves are received, the switching section T/R_SW is turned on. The selecting section MUX outputs a signal of the reflected waves detected by the element chip 200 to the switching section T/R_SW. The switching section T/R_SW outputs the signal of the reflected waves to the receiving section AFE. In this instance, the selecting section MUX is placed in a state of not transmitting the driving voltage from the transmitting section HV_P to the element chip 200. Based on reception instructions from the transmission and reception controlling section CNTL, the receiving section AFE conducts processing of the signal of the reflected waves (for example, amplification processing, A/D conversion processing, or the like), and transmits the processed signal to the processing section 420. The processing section 420 images the signal and causes the display section 440 to display.

The ultrasonic device according to the present embodiment is not limited to a medical ultrasonic diagnostic device such as one described above, but can be applied to various kinds of electronic instruments. For example, as an electronic instrument to which the ultrasonic device is applied, a diagnostic device that conducts non-destructive inspections to the inside of a building, a user interface instrument that detects movement of a user's finger through reflection of ultrasonic waves, and the like may be possible.

While the present embodiment has been explained in detail as above, it will be apparent to those skilled in the art that various changes and modifications can be made herein without substantially departing from the subject matter and the effect of the present invention. Therefore, such changes and modifications are included in the scope of the invention. For example, the terms used in the specification or the drawings at least once together with a different term having a broader or similar meaning can be replaced with the different term in any portion of the specification or the drawings. Also, the configurations and the operations of the ultrasonic device, the ultrasonic probe, the ultrasonic diagnostic device, the electronic instrument, and the like are not limited to the present embodiment, and various changes and modifications are possible.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. An ultrasonic device comprising:
an ultrasonic element group including a plurality of ultrasonic elements, the ultrasonic elements forming "N" columns arranged along a second direction intersecting with a first direction with each of the "N" columns including a plurality of the ultrasonic elements arranged along the first direction, "N" being a natural number that is equal to or more than 2;

a first to an Nth driving electrode lines arranged along the first direction;

a first terminal from which a first driving signal for driving the ultrasonic elements, which is an alternating voltage, is supplied to the ultrasonic elements; and a second terminal from which a second driving signal for driving the ultrasonic elements, which is an alternating voltage, is supplied to the ultrasonic elements, an ith driving electrode line among the first to the Nth driving electrode lines being connected to the ultrasonic elements constituting an ith column among the "N" columns, with "i" being a natural number that is equal to or less than "N", the first terminal being connected to one end of the ith driving electrode line, the second terminal being connected to the other end of the ith driving electrode line.

2. The ultrasonic device according to claim 1, wherein each of the "N" columns includes an "M" number of the ultrasonic elements arranged along the first direction, with the "M" number being a natural number that is equal to or more than 3.

3. The ultrasonic device according to claim 2, wherein the ultrasonic elements are configured such that the number "M" is set equal to or less than a number "a", with the number "a" of the ultrasonic elements having sound pressure distribution characteristics of ultrasonic waves in the first direction, which are output from the ultrasonic element group, that have a half value of a peak sound pressure at center of a column of the ultrasonic elements when input of the first driving signal only to the first terminal is applied.

4. The ultrasonic device according to claim 2, wherein the ultrasonic elements are configured such that the number "M" is set equal to or less than a number "b", with the number "b" of the ultrasonic elements having sound pressure distribution characteristics of ultrasonic waves in the first direction, which are output from the ultrasonic element group, that have a single peak when input of the first driving signal to the first terminal and of the second driving signal to the second terminal is applied, and with a number "b+1" of the ultrasonic elements having the sound pressure distribution characteristics that have double peaks when the input of the first driving signal to the first terminal and of the second driving signal to the second terminal is applied.

5. The ultrasonic device according to claim 1, further comprising
a driving signal output circuit configured to output the first and second driving signals to the first and second terminals, respectively.

6. The ultrasonic device according to claim 5, wherein amplitude of the alternating voltage of the first driving signal output to the first terminal is different from amplitude of the alternating voltage of the second driving signal output to the second terminal.

7. The ultrasonic device according to claim 6, wherein the driving signal output circuit has an output amplifier, a first variable resistance for adjusting amplitude of the first driving signal to the first terminal provided between the output amplifier and the first terminal, and a second variable resistance for adjusting amplitude of the second driving signal to the second terminal provided between the output amplifier and the second terminal.

8. The ultrasonic device according to claim 1, wherein each of the "N" columns includes an "M" number of the ultrasonic elements arranged along the first direction, with the "M" number being a natural number that is equal to or more than 2, and the ultrasonic element group is a group of the ultrasonic elements arranged in a matrix pattern having the "M" number of rows and the "N" columns in which the "N" columns of the ultrasonic elements are arranged.

9. The ultrasonic device according to claim 1, further comprising
a plurality of common electrode lines arranged along the second direction.

10. The ultrasonic device according to claim 9, further comprising
a shared common electrode line commonly-connected to the common electrode lines and arranged along the first direction.

11. The ultrasonic device according to claim 10, further comprising
terminals provided at both ends of the shared common electrode line for supplying a common voltage to the ultrasonic element group.

12. An ultrasonic probe comprising:
the ultrasonic device according to claim 1.

13. An electronic instrument comprising:
the ultrasonic device according to claim 1.

14. A diagnostic device comprising:
the ultrasonic device according to claim 1; and
a display section.

15. A processing device comprising:
the ultrasonic device according to claim 1; and
a driving signal output circuit configured to output the first and second driving signals to the first terminal and the second terminal of the ultrasonic device, respectively.

16. An ultrasonic device comprising:
an ultrasonic element column in which a plurality of ultrasonic elements are arranged;
a driving electrode line connected to the ultrasonic elements;
a first terminal that is connected to one end of the driving electrode line and from which a first driving signal for driving the ultrasonic elements, which is an alternating voltage, is supplied to the ultrasonic elements; and
a second terminal that is connected to the other end of the driving electrode line and from which a second driving signal for driving the ultrasonic elements, which is an alternating voltage, is supplied to the ultrasonic elements.

17. An ultrasonic device comprising:
an ultrasonic element column in which a plurality of ultrasonic elements are arranged; and
a driving electrode line connected to the ultrasonic elements,
driving signals for driving the ultrasonic elements, which are alternating voltages, being supplied to the ultrasonic elements from both ends of the driving electrode line.

* * * * *